US012622997B2

(12) United States Patent
Ji et al.

(10) Patent No.: US 12,622,997 B2
(45) **Date of Patent: *May 12, 2026**

(54) METHOD FOR TREATING ACTIVE BLEEDING USING BIOCOMPATIBLE HEMOSTATIC AND SEALANT COMPOSITIONS

(71) Applicant: Beijing Universal Likang Technology Co., LTD., Beijing (CN)

(72) Inventors: Xin Ji, Shanghai (CN); Xueshen Shi, Beijing (CN); Xiaoguang Zhang, Beijing (CN)

(73) Assignee: Starch Medical, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/644,582

(22) Filed: Apr. 24, 2024

(65) Prior Publication Data

US 2024/0350699 A1 Oct. 24, 2024

Related U.S. Application Data

(63) Continuation of application No. 16/959,994, filed as application No. PCT/CN2019/071108 on Jan. 10, 2019, now Pat. No. 11,998,653.

(30) Foreign Application Priority Data

Jan. 12, 2018 (CN) ......................... 201810031082.4

(51) Int. Cl.

*A61L 24/00* (2006.01)
*A61L 24/04* (2006.01)

(Continued)

(52) U.S. Cl.

CPC ......... *A61L 24/0031* (2013.01); *A61L 24/046* (2013.01); *A61L 24/08* (2013.01);

(Continued)

(58) Field of Classification Search

None

See application file for complete search history.

(56) References Cited

U.S. PATENT DOCUMENTS 471,865 A 3/1892 Howard
576,437 A 2/1897 Elliott (Continued)

FOREIGN PATENT DOCUMENTS

CA 2599082 A1 2/2009
CN 86103931 A 12/1986

(Continued)

OTHER PUBLICATIONS

Natour et al., "Assessment of the effect on blood loss and transfusion requirements when adding a polyethylene glycol sealant to the anastomotic closure of aortic procedures: a case-control analysis of 102 patients undergoing Bentall procedures" J Cardiothorac Surg. 2012; 7: 105. Published online Oct. 8, 2012. doi: 10.1186/1749-8090-7-105.

(Continued)

*Primary Examiner* — Dominic Lazaro
(74) *Attorney, Agent, or Firm* — Novel IP

(57) ABSTRACT

The present specification describes a biocompatible hemostatic composition and a biocompatible tissue sealant, which when used in combination provides a safe and effective method of achieving hemostasis. The biocompatible composition and sealant may be applied either on a surface of the patient's body, or inside the body cavity. The combination (Continued)

may be used to control bleeding from external wounds and internal injuries, as well as to minimize bleeding during surgical procedures.

17 Claims, 13 Drawing Sheets

(51) Int. Cl.
*A61L 24/08* (2006.01)
*A61L 24/10* (2006.01)
*C08L 3/02* (2006.01)
*C08L 5/08* (2006.01)
*C08L 71/02* (2006.01)

(52) U.S. Cl.
CPC ............... *A61L 24/106* (2013.01); *C08L 3/02* (2013.01); *C08L 5/08* (2013.01); *C08L 71/02* (2013.01); *A61L 2400/04* (2013.01)

(56) References Cited

U.S. PATENT DOCUMENTS

| | | | | |
|---|---|---|---|---|
| 881,238 | A | 3/1908 | Sayer | |
| 1,685,280 | A | 9/1928 | Findley | |
| 1,732,566 | A | 10/1929 | Mckendrick | |
| 1,934,793 | A | 11/1933 | Crain | |
| 2,122,234 | A | 6/1938 | Mcauliffe | |
| 2,151,418 | A | 3/1939 | Brown | |
| 2,185,927 | A | 1/1940 | Shelanski | |
| 2,570,774 | A | 10/1951 | Davis | |
| 3,419,006 | A | 12/1968 | King | |
| 4,184,258 | A | 1/1980 | Barrington | |
| 4,616,644 | A | 10/1986 | Saferstein | |
| 5,273,531 | A | 12/1993 | Knoepfler | |
| 5,312,331 | A | 5/1994 | Knoepfler | |
| 5,445,612 | A | 8/1995 | Terakura | |
| 5,599,297 | A | 2/1997 | Chin | |
| 5,800,381 | A | 9/1998 | Ognier | |
| 5,874,500 | A | 2/1999 | Rhee | |
| 5,951,531 | A | 9/1999 | Ferdman | |
| 6,312,725 | B1 | 11/2001 | Wallace | |
| 6,432,069 | B1 | 8/2002 | Godo | |
| 6,610,005 | B1 | 8/2003 | Tao | |
| 7,427,607 | B2 | 9/2008 | Suzuki | |
| 7,547,292 | B2 | 6/2009 | Sheldrake | |
| 8,575,132 | B2 | 11/2013 | Ji | |
| 8,721,582 | B2 | 5/2014 | Ji | |
| 8,827,980 | B2 | 9/2014 | Ji | |
| 8,912,168 | B2 | 12/2014 | Ji | |
| 9,533,005 | B2 | 1/2017 | Ji | |
| 9,629,966 | B2 | 4/2017 | Ji | |
| 9,687,501 | B2 | 6/2017 | Ji | |
| 10,076,590 | B2 | 9/2018 | Ji | |
| 10,195,312 | B2 | 2/2019 | Ji | |
| 11,998,653 | B2 * | 6/2024 | Ji ........................ | A61L 26/0023 |
| 2003/0181917 | A1 | 9/2003 | Gertner | |
| 2004/0096507 | A1 | 5/2004 | Kwang | |
| 2008/0021374 | A1 | 1/2008 | Kawata | |
| 2008/0214989 | A1 | 9/2008 | Kawata | |
| 2009/0062233 | A1 | 3/2009 | Ji | |
| 2010/0035886 | A1 | 2/2010 | Cincotta | |
| 2010/0331232 | A1 | 12/2010 | Barker | |
| 2011/0066132 | A1 | 3/2011 | Ji | |
| 2011/0178495 | A1 | 7/2011 | Ji | |
| 2011/0208158 | A1 | 8/2011 | Sigmon, Jr. | |
| 2011/0224724 | A1 | 9/2011 | Lu | |
| 2013/0046278 | A1 | 2/2013 | Ji | |
| 2013/0090291 | A1 * | 4/2013 | Gulle ..................... | A61K 35/32 514/13.7 |
| 2013/0108671 | A1 | 5/2013 | Mccoy | |
| 2013/0123213 | A1 | 5/2013 | Ji | |
| 2013/0131621 | A1 | 5/2013 | Van Holten | |
| 2013/0255538 | A1 | 10/2013 | Lu | |
| 2014/0207097 | A1 | 7/2014 | Ji | |
| 2014/0369952 | A1 * | 12/2014 | Liu ....................... | C08F 283/02 525/450 |
| 2015/0297520 | A1 | 10/2015 | Kobiki | |
| 2015/0359925 | A1 | 12/2015 | Wang | |
| 2016/0339143 | A1 * | 11/2016 | Ji ............................ | A61K 9/14 |
| 2017/0252479 | A1 | 9/2017 | Ji | |

FOREIGN PATENT DOCUMENTS

| | | | |
|---|---|---|---|
| CN | 1451667 | A | 10/2003 |
| CN | 101091803 | A | 12/2007 |
| CN | 101121041 | A | 2/2008 |
| CN | 101361986 | A | 2/2009 |
| CN | 101455857 | A | 6/2009 |
| CN | 101485897 | A | 7/2009 |
| CN | 101497670 | A | 8/2009 |
| CN | 101785873 | A | 7/2010 |
| CN | 102019028 | B | 4/2011 |
| CN | 102762244 | A | 10/2012 |
| CN | 103957947 | A | 7/2014 |
| CN | 103957948 | A | 7/2014 |
| CN | 103957949 | A | 7/2014 |
| CN | 103957954 | A | 7/2014 |
| CN | 104689380 | A | 6/2015 |
| CN | 105412975 | A | 3/2016 |
| CN | 105536039 | A | 5/2016 |
| CN | 105688265 | A | 6/2016 |
| CN | 106267379 | A | 1/2017 |
| CN | 106474529 | A | 3/2017 |
| CN | 106729775 | A | 5/2017 |
| CN | 106806936 | A | 6/2017 |
| CN | 107349436 | A | 11/2017 |
| EP | 0206697 | A2 | 12/1986 |
| EP | 0290166 | A2 | 11/1988 |
| EP | 1523994 | A1 | 4/2005 |
| EP | 2617792 | A2 | 7/2013 |
| EP | 3228331 | A1 | 10/2017 |
| JP | 2017527416 | A | 9/2017 |
| KR | 20140100245 | A | 8/2014 |
| KR | 20170060054 | A | 5/2017 |
| WO | 2012006247 | A2 | 1/2012 |
| WO | 201403056 | A1 | 1/2014 |
| WO | 2016041443 | A1 | 3/2016 |
| WO | 2018157772 | A1 | 9/2018 |
| WO | 2019134921 | A1 | 7/2019 |
| WO | 2020020114 | A1 | 1/2020 |

OTHER PUBLICATIONS

International Search Report for PCT/CN2015/088844, Dec. 8, 2015.
Database WP1 Week 201068 Thomson Scientific, London, GB; AN 2010-K65387 XP002784440, & CN101785873A (Ji X) Jul. 28, 2010.
N. N. : "Polyox TM WSR 301 Amerchol", The Dow Chemical Company Sales Specification, 2012, XP002784406.
N. N. : "Polyox TM Water Soluble Resins", Dow, Oct. 2013, XP002784441.
International Search Report for PCT/CN2019/071108, Apr. 8, 2019.
International Search Report for PCT/CN2019/097177, Oct. 29, 2019.
ISA, International Search Report and Writeen Opinion for International Patent Application No. PCT/CN2018/077201 with English Translation. Mail Date: May 30, 2018. 10 pages.
University of Central Florida, Chapter 17 Physics of Hearing, 17.7 Ultrasound, Aug. 22, 2016 (Year: 2016).

* cited by examiner

| | | 711<br>Mild bleeding (Oozing) | 712<br>Moderate bleeding | 713<br>Severe bleeding |
|---|---|---|---|---|
| | Protocol | | | |
| 701 | Control group 1<br>PerClot® hemostatic powder - CMS (#66) only | 100%Success | 70% Success | 100% Failed |
| 702 | Control Group 2<br>SuperClot hemostatic powder #51 only | 100%Success | Success ratio 80% | 100% Failed |
| 703 | Control Group 3<br>PEG glue only | 100%Success | 40% success | 100% Failed |
| 704 | Control Group 4<br>(Pullulan polysaccharide) | 100%Failed | 100%Failed | 100%Failed |
| 705 | Test Group 1<br>Hemostatic Powder + Sealant Gel, repeated application | 100%Success | 100%Success | 100%Success |
| 706 | Test Group 2<br>Hemostatic Powder + Sealant Gel | 100%Success | 100 %Success | 100%Success |
| 707 | Test Group 3<br>Hemostatic Powder + PEG sealant powder, repeated application | 100% Success | 100%Success | 100%Success |
| 708 | Test Group 4<br>Hemostatic Powder + PEG sealant powder | 100% Success | 100%Success | 100%Success |
| 709 | Control Group 5<br>CoSeal® PEG glue only | 0 success | 0 success | O success |
| 710 | Control Group 6<br>PerClot Hemostatic powder + CoSeal PEG glue ( method as fig 2) | 100% success | 100% success | 100% success |
| 711 | Control 7<br>PEG powders Only | 0 success | 0 success | O success |

FIG.7

| | Sample ID | 906<br>Gel curing time (second) | 901<br>Mild bleeding (Oozing) | 902<br>Moderate bleeding | 903<br>Severe bleeding |
|---|---|---|---|---|---|
| 904 Control group | | | | | |
| 1 | PerClot® | -- | 100%Success | 70% Success | 100% Failed |
| 2 | PEGs GLUE MODEL A1 | 60 | 40%Success | 100%Failed | 100% Failed |
| 3 | PEGs GLUE MODEL B1 | 20 | 100%Success | 40% Success | 100% Failed |
| 4 | PEGs GLUE MODEL A2 | 30 | 40%Success | 100%Failed | 100% Failed |
| 5 | PEGs GLUE MODEL B2 | 10 | 100%Success | 40% Success | 100% Failed |
| 6 | PEGs GLUE MODEL C1 | 20 | 100%Success | 40% Success | 100% Failed |
| 7 | PEGs GLUE MODEL C2 | 30 | 40%Success | 100%Failed | 100% Failed |
| 8 | PEGs GLUE MODEL D1 | 15 | 100%Success | 40% Success | 100% Failed |
| 9 | PEGs GLUE MODEL D2 | 10 | 40%Success | 100%Failed | 100% Failed |
| 10 | CoSeal® | 60 | 40%Success | 100%Failed | 100% Failed |
| 905 Test Group | | | | | |
| 1 | PerClot®+ MODEL A1 | 15 | 100% Success | 100%Success | 100%Success |
| 2 | PerClot®+ MODEL B1 | 5 | 100% Success | 100%Success | 100%Success |
| 3 | PerClot®+ MODEL A2 | 10 | 100% Success | 100%Success | 100%Success |
| 4 | PerClot®+ MODEL B2 | 3 | 100% Success | 100%Success | 100%Success |
| 5 | PerClot®+ MODEL C1 | 5 | 100% Success | 100%Success | 100%Success |
| 6 | PerClot®+ MODEL C2 | 10 | 100% Success | 100%Success | 100%Success |
| 7 | PerClot®+ MODEL D1 | 5 | 100% Success | 100%Success | 100%Success |
| 8 | PerClot®+ MODEL D2 | 3 | 100% Success | 100%Success | 100%Success |
| 9 | PerClot®+ CoSEAL® | 15 | 100% Success | 100%Success | 100%Success |

FIG.9

| | Sample ID | 1001 Mild bleeding (Oozing) | 1002 Moderate bleeding | 1003 Severe bleeding |
|---|---|---|---|---|
| 1004 Control group | | | | |
| 1 | PerClot® | 100%Success | 70% Success | 100% Failed |
| 2 | PEGs powder P1 | 100%Failed | 100%Failed | 100%Failed |
| 3 | PEGs powder P2 | 100%Failed | 100%Failed | 100%Failed |
| 4 | PEGs powder P3 | 100%Failed | 100%Failed | 100%Failed |
| 5 | PEGs powder P4 | 100%Failed | 100%Failed | 100%Failed |
| 6 | PEGs powder P5 | 100%Failed | 100%Failed | 100%Failed |
| 7 | PEGs powder P6 | 100%Failed | 100%Failed | 100%Failed |
| 8 | PEGs powder P7 | 100%Failed | 100%Failed | 100%Failed |
| 9 | PEGs powder P8 | 100%Failed | 100%Failed | 100%Failed |
| 1005 Test Group | | | | |
| 1 | PerClot®+P1 (3: 1) | 100% Success | 100%Success | 100%Success |
| 2 | PerClot®+P2 (3: 1) | 100% Success | 100%Success | 100%Success |
| 3 | PerClot®+P3 (3: 1) | 100% Success | 100%Success | 100%Success |
| 4 | PerClot®+P4 (3: 1) | 100% Success | 100%Success | 100%Success |
| 5 | PerClot®+P5 (3: 1) | 100% Success | 100%Success | 100%Success |
| 6 | PerClot®+P6 (3: 1) | 100% Success | 100%Success | 100%Success |
| 7 | PerClot®+P7 (3: 1) | 100% Success | 100%Success | 100%Success |
| 8 | PerClot®+P8 (3: 1) | 100% Success | 100%Success | 100%Success |

FIG.10

| | | | 1101 | 1102 | 1103 |
|---|---|---|---|---|---|
| | | Sample ID | Mild bleeding (Oozing) | Moderate bleeding | Severe bleeding |
| 1104 | Control group | | | | |
| | 1 | PA | 100%Failed | 100%Failed | 100%Failed |
| | 2 | PB | 100%Failed | 100%Failed | 100%Failed |
| | 3 | PC | 100%Failed | 100%Failed | 100%Failed |
| | 4 | M1 | 30%Failed | 100%Failed | 100%Failed |
| | 5 | M2 | 30% Success | 100%Failed | 100%Failed |
| | 6 | M3 | 100% Success | 60% Success | 100%Failed |
| | 7 | M4 | 50% Success | 100%Failed | 100%Failed |
| | 8 | M5 | 100% Success | 40% Success | 100%Failed |
| | 9 | M6 | 100% Success | 80% Success | 100%Failed |
| 1105 | Test Group | | | | |
| 1111 | 1 | PA(20%)+PB(10%)+M5(70%) | 100% Success | 100%Success | 100%Success |
| 1112 | 2 | PA(20%)+PC(5%)+M3(75%) | 100% Success | 100%Success | 100%Success |
| 1113 | 3 | PA(10%)+PC(30%)+M2(60%) | 100% Success | 100%Success | 20%Success |
| 1114 | 4 | PA(30%)+PB(10%)+M4(60%) | 100% Success | 100%Success | 60%Success |
| 1115 | 5 | PA(30%)+PB(10%)+M6(60%) | 100% Success | 100%Success | 100%Success |
| 1116 | 6 | PA(25%)+PB(10%)+M1(65%) | 100% Success | 100%Success | 0%Success |

FIG.11

Appendix

| Category | Polysaccharide Name |
| --- | --- |
| Starch-base | hydroxyethyl starch (HES) |
| | CMS(carboxymethyl starch) and its sodium |
| | Tert-amino-ethyl starch |
| | HDMAEP-HES |
| | The aldehyde group hydroxyethyl starch |
| | Carbamyl ethylated carboxymethyl starch |
| | The modified starch of dialdehyde schiff base |
| | hydroxy propyl distarch phosphate |
| | hydroxypropyl carboxymethyl starch |
| | Polyhydroxy acetic acid grafted starch |
| | Acrylamide is grafted with starch |
| | sulfhydryl crosslinked starch |
| | Sulfhydrated beta-cyclodextrin - starch composite microspheres |
| | Dialdehyde starch |
| | cross-linked amino-starch |
| | |
| Cellulose- base | Carboxymethylcellulose，CMC |
| | Hydroxyethyl Cellulose，HEC |
| | hydroxy propyl cellulose |
| | DCMC |
| | Amino carboxymethyl cellulose |
| | amino acid ethyl cellulose |
| | Thiol modified carboxymethyl cellulose （CMC-SH） |
| | Amino hydroxyethyl cellulose |
| | HPMC hydroxypropyl methyl cellulose |
| | |
| Chitosan-based | Sulfhydryl carboxymethyl chitosan |
| | DCMCS |

FIG.12

METHOD FOR TREATING ACTIVE BLEEDING USING BIOCOMPATIBLE HEMOSTATIC AND SEALANT COMPOSITIONS

CROSS-REFERENCE

The present application is a continuation application of U.S. patent application Ser. No. 16/959,994, titled "Method for Treating Active Bleeding by Sequentially Applying a Biocompatible Hemostatic Composition and a Sealant Composition" and filed on Jul. 2, 2020, which is a National Stage application of PCT Application Number PCT/CN2019/071108 under 35 U.S.C. 371, which, in turn, claims the benefit of, and priority to, Chinese Patent Application Number 201810031082.4, filed on Jan. 12, 2018. All of the above applications are hereby incorporated by reference in their entirety.

FIELD

The present specification relates generally to hemostasis and sealing of tissue, and more specifically, to a method that uses biocompatible materials to achieve the functions of hemostasis as well as surgical sealing to control bleeding from a tissue.

BACKGROUND

Surgical operations and trauma may create bleeding wounds, which can bring a risk of excess blood loss. In such situations therefore, it is necessary to apply hemostats to control bleeding in a timely manner. It is common to apply biocompatible, absorbable hemostatic agents directly to bleeding wound sites to achieve hemostasis (cessation of bleeding) in surgical procedures, trauma treatment and home self-rescue. Products commonly used for treating wounds include tissue sealants and hemostats, such as hemostatic powders and dressings including bandages, hemostatic sponges, and gauzes.

Tissue sealants function by solidifying or gelatinizing (gel forming) and/or by interacting with blood to trigger clot formation. Sealants are effective when there is mild bleeding or oozing, such as from a capillary or small vein, in cases of low outflow of blood extruding from a tissue, or as surgical adhesive to seal a tissue after operation. However, when the bleeding is profuse or active, the efficacy of sealants is significantly reduced, as the heavy outflow of blood washes away the sealant gel or glue before it is able to set in at the site and start functioning.

Hemostats such as powders, sponges or gauzes are useful to control the bleeding if it is mild to moderate. However, profuse bleeding requires use of other techniques such as manual (topical) compression in addition to hemostats to achieve cessation of bleeding. For example, U.S. Pat. No. 8,912,168, assigned to Xin Ji, discloses hemostat and sealant products based on modified starch. However, one of the main disadvantages of modified starch based compositions is that the gel formed at the site of application is not strong enough to hold when the flow of blood is high. This is because modified starch alone cannot covalently bond to tissue proteins, and is therefore unsatisfactory as a sealant and shows poor efficacy in case of profuse bleeding.

U.S. Pat. Nos. 5,874,500 and 6,312,725, both assigned to Cohesion Technologies, dis close polyethylene glycol (PEG) and fibrin glue based sealant compositions. PEG and fibrin glue both have the capability of forming cross links with tissue proteins at the site of bleeding. However, both PEG and fibrin glue work ideally on sealing oozing wounds (exhibiting mild bleeding) or on wounds which are dry (bleeding has stopped). For PEG based compositions, gel forming takes some time so when there is active bleeding the blood tends to wash away the applied composition before it is able to form a gel and set in to seal the wound.

In general, a clinician needs to use both a hemostat and a sealant to treat the wound when there is active bleeding, especially when bleeding is accompanied by internal injury or trauma, or needs to be minimized during a surgical procedure. Doctors also frequently need to use surgical sealants within "wet" wounds when there is bleeding and/or extrudates are coming out from the wounds.

There is therefore a need for a product which provides the functions of both hemostasis and wound sealing in an effective and timely manner, even when the bleeding is profuse. Further, the product should be convenient to use and capable of being applied topically on a bleeding wound surface outside or within the body cavity. Such a hemostatic product must be capable of being applied directly or by means of ancillary devices, such as a specific delivery device or endoscope, so as to achieve rapid and effective hemostasis, seal the wound and avoid re-bleeding.

SUMMARY

In some embodiments, the present specification discloses a method of using a combination of a biocompatible hemostatic product and a biocompatible sealant product to treat a bleeding wound within or on a mammal, comprising: applying a first amount of said biocompatible hemostatic product to said bleeding wound; applying a second amount of said biocompatible sealant product to the bleeding wound, wherein said first amount and said second amount in combination are sufficient to cause at least one of: hemostasis in said bleeding wound, wound sealing in said wound, reducing exudation of said bleeding wound, promoting tissue healing of said wound, protecting a surface of said wound, and avoiding infection of said wound.

In some embodiments, the present specification discloses a method of using a combination of a biocompatible hemostatic product and a biocompatible sealant product to treat a bleeding wound in a patient's body, comprising: applying a first amount of the biocompatible hemostatic product to said bleeding wound; and after applying the first amount of the biocompatible hemostatic product to the bleeding wound, applying a second amount of the said biocompatible sealant product to the bleeding wound, wherein said first amount and said second amount are sufficient to cause at least one of hemostasis in said bleeding wound, sealing said wound, reducing exudation of said bleeding wound, promoting tissue healing around said wound, protecting a surface of said wound, and avoiding infection of said wound. The first amount of the biocompatible hemostatic product and the second amount of the said biocompatible sealant product may be repeatedly and alternately used as needed until desired effect is achieved.

In some embodiments, the present specification discloses a method of using a combination of a biocompatible hemostatic product and a biocompatible sealant product to treat a bleeding wound in a patient's body, comprising: applying a second amount of the said biocompatible sealant product to the bleeding wound; after applying the second amount of the said biocompatible sealant product to the bleeding wound, applying a first amount of the biocompatible hemostatic product to said bleeding wound; wherein said first amount and said second amount are sufficient to cause at least one of hemostasis in said bleeding wound, sealing said wound, reducing exudation of said bleeding wound, promoting tissue healing around said wound, protecting a surface of said wound, and avoiding infection of said wound. The first amount of the biocompatible hemostatic product and the second amount of the said biocompatible sealant product may be repeatedly and alternately used as needed until desired effect is achieved.

In some embodiments, the present specification discloses a method of using a combination of a biocompatible hemostatic product and a biocompatible sealant product to treat a bleeding wound in a patient's body, comprising: applying a first amount of the biocompatible hemostatic product to said bleeding wound; and simultaneously applying a second amount of the said biocompatible sealant product to the bleeding wound, wherein said first amount and said second amount are sufficient to cause at least one of hemostasis in said bleeding wound, sealing said wound, reducing exudation of said bleeding wound, promoting tissue healing around said wound, protecting a surface of said wound, and avoiding infection of said wound.

In some embodiments, the present specification discloses a method of using a combination of a biocompatible hemostatic composition and a biocompatible sealant composition to treat a bleeding wound in a patient's body, comprising: mixing a first amount of the biocompatible hemostatic composition with a second amount of the biocompatible sealant composition; and after mixing the first amount of the biocompatible hemostatic composition with a second amount of the biocompatible sealant composition, applying the mixture of said biocompatible hemostatic and said biocompatible sealant compositions to said bleeding wound, wherein said first amount and said second amount are sufficient to cause at least one of hemostasis in said bleeding wound, sealing said wound, reducing exudation of said bleeding wound, promoting tissue healing around said wound, protecting a surface of said wound, and avoiding infection of said wound.

The following optional embodiments are applicable to all of the products, compositions and other embodiments described above and throughout the specification.

Optionally, said biocompatible hemostatic product comprises at least one of a biocompatible hydrophilic hemostatic modified starch, cellulose, cellulose derivatives, chitosan, chitosan derivatives, alginate and alginate derivatives.

Optionally, said biocompatible sealant product comprises at least one of: at least one of a biocompatible modified starch gel, a polysaccharide glue, a fibrin glue, a thrombin glue, and a bio-glue; and at least one sugar selected from polysaccharides, oligosaccharides and oligosaccharides, such as Pullulan polysaccharide, maltose, pre-gelatinized starch, Dextran, hydroxypropyl distarch phosphate, sodium carboxymethyl starch, crosslinked carboxymethyl starch, hydroxyethyl starch, oxidized starch, and grafted starch.

Optionally, said biocompatible sealant product comprises at least one of: at least one polymeric compound selected from N-butyl cyanoacrylate, PEG/PEO (polyethylene glycol/polyethylene oxide), PVA (polyvinyl acetate), PVP (polyvinylpyrrolidone); at least one protein, such as corn peptide; and, a material comprising a combination of two components to form a gel.

Optionally, said at least one protein comprises a corn peptide.

Optionally, said combination of two components to form the gel comprises at least one of 1) fibrin glue and bio-glue, 2) a combination of PEG and derivatives thereof, 3) carboxymethyl starch and glycerol in combination with a medium molecular weight PVA solution, 4) carboxymethyl starch and soybean oil in combination with a low molecular weight PVA solution, and 5) carboxymethyl starch and glycerol in combination with a hydroxypropyl distarch phosphate (HPDSP) solution.

Optionally, said biocompatible hemostatic product is in the form of a powder.

Optionally, said biocompatible sealant product is in the form of a gel, glue, paste or liquid.

Optionally, the particle sizes of said biocompatible hemostatic powder ranges from 1-4000 micrometers.

Optionally, the particle sizes of said biocompatible hemostatic powder ranges from 10-1000 micrometers.

Optionally, the particle sizes of said biocompatible hemostatic powder ranges from 10-500 micrometers.

Optionally, the particles of said biocompatible hemostatic powder have a water absorbency capacity of more than two times of the particles' own weight.

Optionally, the particles of said biocompatible hemostatic powder have a water absorbency capacity ranging from 5 to 100 times of the particles' own weight.

Optionally, the particles of said biocompatible hemostatic powder have a water absorbency capacity ranging from 5 to 50 times of the particles' own weight.

Optionally, the particles of said biocompatible hemostatic powder have a water absorbency rate of up to 50% of the particles' full capacity within a first 30 seconds of contact with water.

Optionally, the particles of said biocompatible hemostatic powder have a water absorbency rate of up to 10% of the particles' full capacity within a first 30 seconds of contact with water.

Optionally, the particles of said biocompatible hemostatic powder have a water absorbency rate of up to 20% of the particles' full capacity within a first 30 seconds of contact with water.

Optionally, the particles of said biocompatible hemostatic powder have a molecular weight of 3,000 Daltons or more.

Optionally, the particles of said biocompatible hemostatic powder have a molecular weight of 5,000 Daltons or more.

Optionally, the particles of said biocompatible hemostatic powder have a molecular weight ranging from 5,000 to 2,000,000 Daltons or more.

Optionally, said biocompatible sealant product is configured to adhere to the bleeding wound by formation of covalent bonds with tissue proteins.

Optionally, said biocompatible hemostatic gel is adapted to gelatinize in approximately less than 1 minutes upon contact with the bleeding wound.

Optionally, said biocompatible hemostatic gel is adapted to gelatinize in approximately less than 3 minutes upon contact with the bleeding wound.

Optionally, said biocompatible hemostatic gel is adapted to gelatinize in approximately less than 5 minutes upon contact with the bleeding wound.

Optionally, the bleeding wound is located in tissue of at least one of the mammal's respiratory tract, digestive tract, genital tract, and gastrointestinal tract.

Optionally, the biocompatible modified starch is selected from a group consisting of at least one of: a pre-gelatinized starch, an acid modified starch, an esterified starch, an etherified starch, a graft starch, a cross-linked starch and a composite modified starch.

Optionally, the biocompatible hydrophilic hemostatic modified starch is at least one of a carboxymethyl starch and a sodium salt thereof.

Optionally, applying said first amount and said second amount are repeated until complete hemostasis is achieved.

In some embodiments, the present specification discloses a product for treating a bleeding wound in a human or animal body, said product comprising: a first amount of a biocompatible hemostatic product; and a second amount of a biocompatible sealant product, wherein, when applied to said bleeding wound, said first amount and said second amount are sufficient to cause at least one of hemostasis in said bleeding wound, sealing said wound, reducing exudation of said bleeding wound, promoting tissue healing around said wound, protecting a surface of said wound, and avoiding infection of said wound.

Optionally, said biocompatible hemostatic product is in the form of a powder and comprises carboxymethyl starch (CMS) and the sodium salt thereof.

Optionally, said biocompatible sealant product is in the form of a powder and comprises polyethylene glycol (PEG).

Optionally, the particle sizes of said biocompatible hemostatic powder ranges from 1-4000 micrometers.

Optionally, the particle sizes of said biocompatible hemostatic powder ranges from 10-1000 micrometers.

Optionally, the particle sizes of said biocompatible hemostatic powder ranges from 10-500 micrometers.

Optionally, the particles of said biocompatible hemostatic powder have a water absorbency capacity of more than two times of the particles' own weight.

Optionally, the particles of said biocompatible hemostatic powder have a water absorbency capacity ranging from 5 to 100 times of the particles' own weight.

Optionally, the particles of said biocompatible hemostatic powder have a water absorbency capacity ranging from 5 to 50 times of the particles' own weight.

Optionally, particles of said biocompatible hemostatic powder have a water absorbency rate of up to 50% of the particles' full capacity within a first 30 seconds of contact with water.

Optionally, the particles of said biocompatible hemostatic powder have a water absorbency rate of up to 10% of the particles' full capacity within a first 30 seconds of contact with water.

Optionally, the particles of said biocompatible hemostatic powder have a water absorbency rate of up to 20% of the particles' full capacity within a first 30 seconds of contact with water.

Optionally, particles of said biocompatible hemostatic powder have a molecular weight of 3,000 Daltons or more.

Optionally, the particles of said biocompatible hemostatic powder have a molecular weight of 5,000 Daltons or more.

Optionally, the particles of said biocompatible hemostatic powder have a molecular weight ranging from 5,000 to 2,000,000 Daltons or more.

Optionally, particles of said polyethylene glycol (PEG) comprise functional groups crosslinked with other particles of said polyethylene glycol (PEG).

Optionally, particles of said polyethylene glycol (PEG) have a molecular weight of less than 20,000 Daltons.

Optionally, particles of said polyethylene glycol (PEG) have a molecular weight of less than 60,000 Daltons.

Optionally, particles of said polyethylene glycol (PEG) have a molecular weight of less than 100,000 Daltons.

Optionally, particles of said polyethylene glycol (PEG) have at least one functional group adapted to bond to protein molecules.

Optionally, particles of said polyethylene glycol (PEG) have at least one functional group adapted to bond to amino acid molecules.

Optionally, particles of said polyethylene glycol (PEG) have at least one functional group adapted to bond with other particles of said polyethylene glycol (PEG) and at least one functional group adapted to bond with tissue proteins.

Optionally, said product is adapted to gelatinize in approximately less than 3 minutes upon contact with the bleeding wound.

Optionally, said product is adapted to absorb up to 10% of its maximum absorption capacity within a first 10 seconds of application to the bleeding wound.

Optionally, said product is adapted to absorb at least 20% of its maximum absorption capacity within a first 30 seconds of application to the bleeding wound.

Optionally, said product is adapted to absorb at least 50% of its maximum absorption capacity within a first 60 seconds of application to the bleeding wound.

Optionally, a proportion of said biocompatible hemostatic product is in a range of 5% to 95% and a proportion of said biocompatible sealant product is in a range of 95% to 5%.

Optionally, a proportion of said biocompatible hemostatic product is in a range of 65% to 85% and a proportion of said biocompatible sealant product is in a range of 40% to 15%.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 7 is a table summarizing the results of a controlled laboratory experiment to determine the efficacy of compositions of the present specification;

FIG. 9 is a table summarizing the results of a controlled laboratory experiment to determine the efficacy of some compositions of the present specification;

FIG. 10 is a table summarizing the results of another controlled laboratory experiment to determine the efficacy of some compositions of the present specification;

FIG. 11 is a table summarizing the results of another controlled laboratory experiment to determine the efficacy of some compositions of the present specification; and FIG. 12 provides an appendix with a list of polysaccharide powders that may be used in the modified starch based compositions of the present specification.

DETAILED DESCRIPTION

Figure 1:
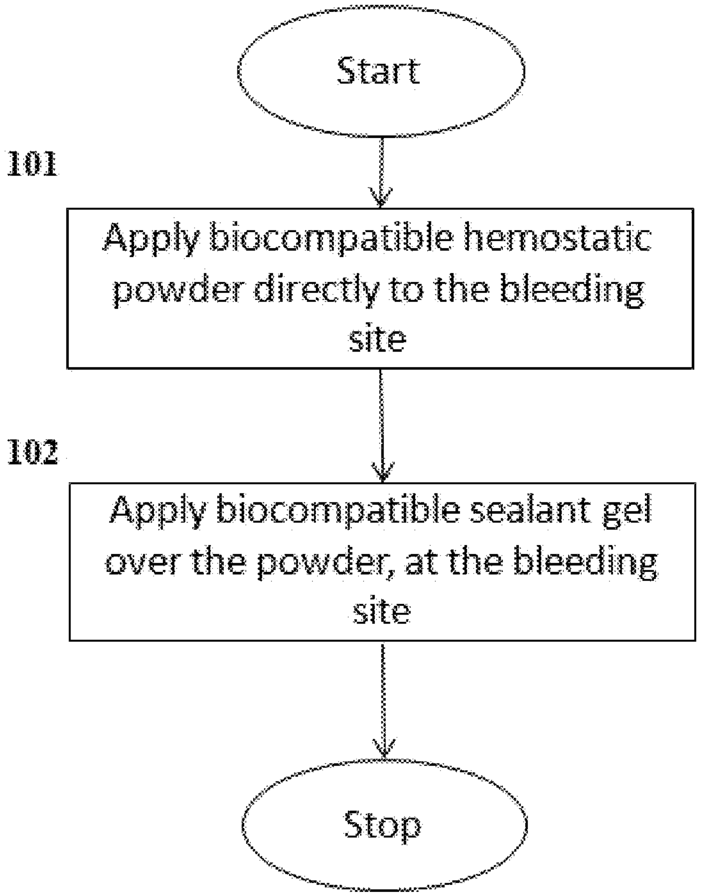
FIG. 1 is a flowchart illustrating steps for an exemplary method of use for the biocompatible hemostatic powder and sealant gel, according to an embodiment of the present specification.

According to some embodiments, the present specification discloses biocompatible compositions and methods of use thereof to simultaneously control active bleeding and achieve hemostasis and sealant function. In an embodiment, hemostasis is achieved immediately and effectively when the biocompatible hemostat composition of the present specification comes into contact with blood on wound sites.

According to some embodiments, a biocompatible hemostatic composition is used in combination with a biocompatible sealant, such that the composition enhances the efficacy of the sealant to achieve both hemostasis and wound sealing when active bleeding occurs from a wound or surgical site. In some embodiments, the biocompatible hemostatic composition is in powder form and is used in combination with a biocompatible sealant composition in glue or gel form. The advantages of this combination, compared to existing hemostatic methods and compositions known in the art, include faster gel forming, and hence wound sealing, due to powder absorbing water from the glue; reducing the amount of hemostatic powder and glue used, compared to when either of them is used independently; enhancing the efficacy of hemostasis, particularly for active/perfuse bleeding when the use of either powder or glue independently does not achieve satisfactory hemostasis; and achieving the functions of both hemostasis and sealant with a single combination.

In some embodiments, the present specification provides blends of biocompatible hemostat compositions, entirely in powder form. The powder blends obviate the need for preparation time, which is required when using a hemostatic composition in combination with a sealant glue or gel. This is an advantage in critical situations, where bleeding needs to be stopped urgently, in addition to being convenient for surgeons or medical professionals as the powder blends are ready to use. In one embodiment, the powder blends can be readily administered inside the body using a minimal invasive endoscope. In one embodiment, powder blends provide a longer shelf life and ease of storage compared to gel based compositions.

In one embodiment, the present specification overcomes the drawbacks occurring when individually using modified starch based products and polyethylene glycol (PEG) based products, by providing compositions that combine the properties of modified starch and PEG polymers to effectively achieve both hemostasis and sealing of wounds with heavy bleeding. In one embodiment, a modified starch based composition is combined with a PEG based composition such that the resulting composition exhibits increased adhesiveness against high blood flow, on account of the polymers forming covalent bonds to the tissue at the bleeding site. The resulting composition is also hydrophilic, as the modified starch components concentrate the blood almost immediately and absorb the water/fluid from the PEG based composition to accelerate gel formation, and increase the viscosity and/or adhesiveness of the formed gel. In one embodiment, the compositions which combine the properties of modified starch and PEG polymers are pre-mixed. In another embodiment, the present specification provides methods for mixing the starch and polymer based compositions on site.

It should be appreciated that in the methods disclosed herein, multiple types of different sealants may be applied and multiple types of hemostatic products may be applied. In particular, typically at least two different types of PEG powders are applied.

The biocompatible compositions of the present specification can be safely used for achieving hemostasis and effective wound sealing in cases of various types of active or severe bleeding, including but not limited to trauma, open surgery, minimally invasive surgery, gastrointestinal bleeding, and body fluid leakage of a certain pressure. Further, the compositions of the present specification may be applied to bleeding wounds or sites on the surface or inside of organs and mucosa surface of humans or animals.

One of ordinary skill in the art would appreciate that direct application of PEG-based hemostatic or sealant powder to a wound or tissue is not known in the art. Normally, PEG powders are required to be mixed with certain PH (acid or base) solutions separately and then two or more PEG solutions (at different pH) are mixed together for cross-linking of functional groups of PEG and gel formation (acting as tissue sealant). In addition, application of PEG powders directly to a wound site is not effective for cross-linking to achieve satisfied hemostasis or a sealant effect, due to influence of pH.

Rather, the prior art discloses forming a glue or gel with the hemostatic or sealant powder and then applying or spraying the prepared gel/glue to the site of bleeding. In contrast, the biocompatible compositions of the present specification can be safely applied directly to bleeding sites inside or outside the body. In embodiments, the sealant effect of the present specification can be achieved by application in situ (directly on the body site) without prior preparation or mixing.

As mentioned above, in some embodiments, the present specification uses the hydrophilic modified starch based hemostatic compositions in combination with PEG-based sealant compositions in a manner such that the hemostatic compositions accelerate gel forming by rapidly concentrating PEG compositions to get faster curing time. This is demonstrated by a series of tests, the results of which are summarized in the tables of FIGS. 9 and 10. In one embodiment, the present combination of compositions achieved 100% success in controlling mild, moderate and severe bleeding, where prior art compositions failed.

Further as mentioned above, the present specification also envisages new composition blends created by chemically crossing functional groups in PEG-based compositions with starch molecules of modified starch-based compositions. For example, in one composition, at least one arm (functional group) of a PEG polymer may be crosslinked with modified starch molecules. In another exemplary composition, at least one arm (functional group) of a PEG polymer may be crosslinked with —SH group of proteins. It should be noted herein that the PEG polymers may contain at least four arms or functional groups available for bonding. In one embodiment, the blends further comprise amino acids and/or other chemicals to increase the efficacy of the hemostatic and sealant products.

The following definitions are provided to further describe various aspects of the preferred embodiments of the present invention.

As used in various embodiments of the present specification, the degree of bleeding is defined qualitatively, wherein "mild" bleeding refers to blood oozing from a capillary; "moderate" bleeding is defined as when a wound site starts bleeding again immediately after wiping clean with a gauze; and "severe" bleeding is defined as that which cannot be controlled by wiping clean with gauze, and needs the use of a suction device.

In embodiments, the degree of bleeding is determine by clinical definitions and are as follows:

For severe bleeding, any one of the following may be true:
- Blood is pumping from the wound.
- The bleeding does not stop or slow down with pressure.
- Blood is quickly soaking through bandage after bandage.

With moderate bleeding, any of these may be true:
- The bleeding slows or stops with pressure but starts again if you remove the pressure.
- The blood may soak through a few bandages, but it is not fast or out of control.

With mild bleeding, any of these may be true:
- The bleeding stops on its own or with pressure.
- The bleeding stops or slows to an ooze or trickle after 15 minutes of pressure. It may ooze or trickle for up to 45 minutes.

The term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface). Accordingly, "gelation time", also referred to herein as "gel time", refers to the time it takes for a composition to become non-flowable under modest stress. This is generally exhibited as achieving a gel strength, G', of greater than or equal to 102 dynes/cm$^2$ in less than 1 minute. Additionally, "gel curing time" is defined as the time required for a glue to go from liquid to solid.

The term "hemostat" or "hemostatic agent" refers to a substance used to control bleeding or promote hemostasis.

The term "sealant" refers to a substance used to block the passage of fluids through the surface or via openings.

The term "surgical sealant" refers to a substance that when in contact with blood, is absorbable and degradable by human tissue and has enhanced tissue adhering properties, therefore sealing the bleeding surface.

The term "biocompatible surgical sealant" refers to a substance that is capable of forming a protective layer of colloid or film on a wound surface to seal and prevent drainage of blood, tissue fluids, lymph fluid, cerebrospinal fluid, bile, gastric fluid, or and other intestinal fluids resulting from surgery and trauma treatment.

The term "biodegradable" refers to the ability of the compositions of the present specification to be degraded or broken down (decomposed into smaller molecules owing to enzymatic action with the human body, which are then either absorbed by the body or eliminated via the kidney (urine).

The term "cohesive strength" refers to the ability of the compositions of the present invention to remain intact, i.e., not rupture, tear or crack, when subjected to physical stresses or environmental conditions. Cohesive strength is sometimes measured as a function of "burst strength".

The term "adhesive strength" refers to the ability of the compositions of the present invention to be able to remain attached to the tissues at the site of administration when subjected to physical stresses or environmental conditions.

The term "polymer" refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure.

The term "synthetic polymer" refers to polymers that are not naturally occurring and that are produced by chemical or recombinant synthesis. As such, naturally occurring proteins such as collagen and naturally occurring polysaccharides such as hyaluronic acid are specifically excluded. Proteins such as synthetic collagen, and carbohydrates such as synthetic hyaluronic acid, and their derivatives, are included.

In some embodiments, the biocompatible compositions of the present specification may be delivered or applied via an endoscope or endoscope based delivery device. An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures. Endoscopes may be categorized according to specific applications, such as cystoscopy, colonoscopy, laparoscopy, bronchoscopy, gastrointestinal endoscopy and others.

It should be appreciated that the methods disclosed herein, specifically the application of one or more biocompatible hemostatic products and one or more biocompatible sealant products to a bleeding wound, is performed during the same, or during a single, operative procedure. The term "operative procedure" may be defined as a medical procedure involving an in vivo application of one or more tools to a living organism.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature, component of formulation described in association with a specific embodiment may be used and implemented with any other embodiment unless clearly indicated otherwise.

The present specification provides a number of biocompatible, biodegradable, hemostatic, hydrophilic and sealant compositions which may be used individually or in combination to achieve rapid and effective hemostasis and wound sealing. The compositions include powder, gel, glue, paste or liquid form. The compositions of the present specification may be applied to humans as well as animals or mammals.

Composition 1

In an embodiment, the present specification provides a biocompatible material, preferably in the form of a powder, comprising a biocompatible modified starch. In an embodiment, the biocompatible modified starch is pre-gelatinized. In one embodiment, the modified starch used in the biocompatible powder composition contains compounds from a hydrophilic group selected from carboxyethyl, carboxymethyl, hydroxyethyl, and hydroxymethyl.

As known in the art, starch is a glucosan, and at room temperature, raw starch is generally not soluble in water, nor does it readily absorb water. Raw starch normally absorbs water at temperatures above 60 degrees C. and swells to an adhesive, translucent and colloidal solution. There are two types of glucose chains in starch, including a simple chain called amylose and a complex branched form called amylopectin. The diameter range of starch grains is normally between 1 and 100 micrometers and the average diameter is from 15 to 30 micrometers. Natural raw starch has minimal hemostatic characteristics because starch grains are small and light and the hydrophilic properties are unsatisfactory at room temperature.

Therefore, raw starch is processed through physical and chemical modifications to obtain modified starch, which has characteristics and properties suitable for the present application. The modification process involves cutting, rearranging, crosslinking or adding other chemical function groups that change the structure of the raw starch molecular chain or glucose units. For example, by carboxylation modification, or hydroxylation modification, the starch captures hydrophilic groups in its molecular structure and obtains hydrophilic properties, as described in greater detail below. By using bifunctional or polyfunctional chemical agents to cross-link the raw starch macromolecules or grafting external macromolecular hydrophilic groups to the raw starch, the starch acquires enhanced hydrophilic properties and viscosity/adhesiveness in a water solution.

U.S. Pat. No. 8,912,168, which is herein incorporated by reference in its entirety, provides formulations for using modified starch as a biocompatible hemostatic material with mechanisms that include dissolving or swelling in water and the subsequent formation of adhesive glue or adhesive gel. The mechanism further includes a modified starch acquisition of hydrophilic groups within its molecular chains through the modification process. When the hydrophilic and enhanced adhesive modified starch is applied to bleeding wound sites, it rapidly absorbs water in the blood and concentrates blood components. Meanwhile, this interaction creates an adhesive matrix formed with the blood and plasma which adheres to the bleeding wound, mechanically seals the broken blood vessels and stops bleeding.

In one embodiment, the modified starch material according to the present specification includes starch modified physically, chemically, naturally, or enzymatically, and starch modified repeatedly with at least one of the above methods or a combination of two or more of the above methods.

As known in the art, physical modification is the process which produces modified starch with the desired properties and functions, by physically changing the microcrystalline starch structure through heating, extrusion, and irradiation. Specifically, physically modified starch includes of pre-gelatinized starch (α-starch), gamma-ray, microwave or high frequency radiation starch, mechanically milled starch, and steam treated starch.

Raw starch can be pre-gelatinized through solely a physical modification process without adding any chemical agents and can become a hemostatic material with enhanced hydrophilic and adhesive properties. Physically modified starch, in one embodiment, is a pre-gelatinized starch treated solely with spray drying or an irradiation process and is safe as a bio-absorbable, hemostatic material since it is not treated with any chemical agents. The starch can be pre-gelatinized by the following physical modifying processes: a) dry-process, such as an extrusion process and a roller process; b) wet-process, such as a spray drying process. Specifically, after heating the raw starch in combination with a measured amount of water, starch granules swell to a pasty substance and regularly arranged micelle of starch are broken, crystallites disappear, and the resulting composition is easily degraded under the process of amylase. The pre-gelatinized starch is able to swell and/or dissolve in cold or room temperature water and form an adhesive paste with a retrogradation which is lower than that of raw starch, affording easier handling during the production process.

In embodiments, the pre-gelatinized starch of the present specification is safe, non-toxic, and has no adverse side effects. The pre-gelatinized starch is readily degraded and metabolized by enzymes in the body. The pre-gelatinized material of the present specification is safe and biocompatible.

The chemical modification process of the present specification includes acidolysis, oxidation, esterification, etherification, cross-linking, chemical agent grafting, or a combination of modification processes including at least two of the above processes, or one of the above modifying processes performed at least twice.

In embodiments, of the present specification, by adding a functional group on the raw starch glucose units with chemical agents, e.g. by carboxylation modification, or hydroxylation modification, the starch captures hydrophilic groups in its molecular structure and obtains hydrophilic properties. By using bifunctional or polyfunctional chemical agents to cross-link the raw starch macromolecules or grafting external macromolecular hydrophilic groups to the raw starch, the starch acquires enhanced hydrophilic properties and viscosity/adhesiveness in a water solution. The viscosity of modified starch relates to the raw starch origin and the degree of substitution of external and cross-linked or grafted functional groups. When contacting blood, the hydrophilic and adhesive properties of the modified starch of the present invention produce a "starch-blood coagulation matrix" with strong adhesive characteristics which can seal wounded tissue and stop bleeding. In addition, the interaction between the formed blood coagulation matrix and the functional groups of tissue proteins causes the "starch-blood coagulation matrix" to adhere to and seal the wounded tissue, resulting in hemostasis.

In an embodiment, a first biocompatible hemostatic composition of the present specification comprises a biocompatible modified starch hemostat, which includes but is not limited to a pre-gelatinized starch, and one or more of other biocompatible hemostatic materials such as, but not limited to, cellulose and its derivative, oxidized cellulose, oxidized regenerated cellulose, alginate and chitosan. As known in the art, the hemostatic mechanism of cellulose and its derivatives involves the concentration of blood components through the hygroscopic activity of cellulose, which stimulates blood coagulation as the carboxyl material combines with hemoglobin Fe to produce acidic hematin in the blood. The resulting brown gel seals capillary vessels and promotes hemostasis. Chitosan is made from the crushed shells of crustaceans. Chitosan has rapid hydrophilic capability and can activate the blood coagulation mechanism through its strong ionic charge. In one embodiment, the biocompatible hemostatic and hydrophilic composition further comprises Alginate hydrogel, which is a biomaterial and finds wide applications in wound healing due to its structural similarity to extracellular matrices of living tissues.

In one embodiment, the weight ratio or proportion of the biocompatible modified starch to other biocompatible hemostatic materials in the first biocompatible composition is in the range of 1:99 to 99:1. Specifically, the weight ratio between the modified starch and other biocompatible hemostatic materials is preferably one of: 95:5, 90:10, 85:15, 80:20, 75:25, 70:30, 65:35, 60:40, 55:45, 50:50, 45:55, 40:60, 35:65, 30:70, 2575, or 20:80, or any increment therein.

In one embodiment, the biocompatible composition of the present specification is in powder form and comprises particles ranging in size from 0.5 micrometer to 4,000 micrometers, preferably in the range of 50-1000 micrometers. In one embodiment, the composition has a water absorption capacity of 5-1000 times of its own weight, preferably in the range of 5-100 times, and the rate of absorption of blood is up to 50% of its full absorption capacity within the first 30, 60, 120 seconds of contact with the blood. In one embodiment, the present composition absorbs up to 10% of its maximum absorption capacity within first 10 seconds of application, more than 20% within the first 30 seconds, and 50% of its full capacity within 60 seconds of application. In one embodiment the viscosity of the biocompatible composition in a 2% water solution, at 37 degrees C. is 10 mPa·s, determined using a viscometer test. In one embodiment, the biocompatible modified starch particles in the composition exhibit a viscosity of not lower than 30 mPa·s, in a 6.67% water suspension at 37 deg. C.

In one embodiment, the biocompatible modified starch particles in the composition have a grain diameter of 1 to 1000 micrometers. In one embodiment, the biocompatible modified starch particles have a molecular weight of 3,000 Daltons or more, or 5,000 Daltons or more, or 15,000 Daltons or more.

In one embodiment, the biocompatible hemostatic powder comprises one or more of carboxymethyl starch (CMS) hemostatic powder, crosslinked CMS hemostatic powder, pre-gelatinized, and gelatinized modified starch hemostatic powder.

FIG. 12 provides an appendix with a list of various polysaccharide powders that may be used in the modified starch based compositions of the present specification. The table 1200 of FIG. 12 provides a list of starch based, cellulose based and chitosan based products.

Composition 2

In an embodiment, a second biocompatible composition of the present specification comprises a sealant, preferably in the form of a gel, paste, liquid or glue, comprising a combination of natural hemostatic polysaccharides such as biocompatible modified starch gel/glue, cellulose glue and fibrin glue, and synthetic hemostatic glues such as HA (hyaluronic acid) gel/glue, PEG glue, PEO glue, and synthetic polymer glue/gel.

As known in the art, fibrin glues consist mainly of clotting factors such as fibrinogen and thrombin. The hemostatic action relies mainly on the activation of fibrinogen by the thrombin to promote coagulation cascade. Fibrin glues demonstrate weak adhesion when applied to wet, bleeding tissue and may be ineffective in the presence of active bleeding. Further, fibrin glues require special mixing, timing and storage condition. Poly(ethylene glycol) (PEG), otherwise known as poly(oxyethylene) or poly(ethylene oxide) (PEO), is a synthetic polyether that is readily available in a range of molecular weights. Materials with Mw<100,000 are usually called PEGs, while higher molecular weight polymers are classified as PEOs. PEO is a commonly used medical polymer and often used as an excipient or a plasticizer suitable for the medicaments in manufacturing medical binders or tablets. Small molecular weight Polyethylene glycol (PEG) (preferably under 20,000 Daltons) is biodegradable and can be eliminated via urine from human body. PEG has been used to make surgical sealant/glue.

Hemostatic glue (e.g., hydrogel and sealant glue) prepared with polysaccharide or synthetic polymer can be applied topically on the sutured skin wound or surgical wound in the body caused by trauma, surgeries for the purpose of hemostasis, protecting the wound, avoiding exudation of fluid and preventing infection.

In one embodiment, the sealant gel/glue of the present specification comprises a combination of i) sugar, that is, polysaccharides, oligosaccharides and oligosaccharides, such as Pullulan polysaccharide, maltose, pre-gelatinized starch, Dextran, hydroxypropyl distarch phosphate, sodium carboxymethyl starch, crosslinked CMS, hydroxyethyl starch, oxidized starch, and grafted starch; ii) polymeric compounds such as N-butyl cyanoacrylate, PEG/PEO (polyethylene glycol/polyethylene oxide), PVA (polyvinyl acetate), PVP (polyvinylpyrrolidone); iii) protein, such as corn peptide; and iv) a material comprising a combination of two components to form a gel, such as fibrin glue, bio-glue, a PEG and PEG combination, CMS and glycerol in combination with 5% PVA (medium molecular weight) solution, CMS and soybean oil in combination with 5% PVA (low molecular weight) solution, CMS and glycerol in combination with 5% HPDSP (hydroxypropyl distarch phosphate).

The sealant compositions of the present specification, as described above, therefore aims to combine the natural hemostatic agents with synthetic or polymer based hemostats to achieve a biocompatible sealant that can be safely applied even to internal wounds or to internal tissue during surgery. The compositions, when applied inside the body, are biodegradable and absorbable.

In one embodiment, the present sealant composition demonstrates a high degree of adhesiveness to tissue, owing to either action of clotting substances like thrombin and fibrin which trigger/accelerate the clot cascade or due to chemical bonding manifested by substances such as PEG/PEO and cross-linking to tissue proteins.

As known in the art, the viscosity of a polymer based composition may vary according to the type of polymers in the composition. In one embodiment, the biocompatible sealant gel of the present specification exhibits a minimum viscosity of 557 mPa·S for a 6.67% solution of CMS powder at a temperature of 37 deg C. In one embodiment, the time it takes for the sealant to form a gel at the site of bleeding is less than 60 seconds, or three minutes, or five minutes, or ten minutes, preferably, less than three minutes. In other words, on application to a wound site, the sealant is gelatinized in less than three minutes, on account of forming crosslinks. In one embodiment, crosslinks are formed between the polymeric components of the gel. Crosslinks are also formed by means of covalent bonds forming between the components of sealant gel and hemoglobin of blood, proteins and collagen of the tissue on which the gel is applied. In one mechanism, two polymer components form crosslinks each other, followed by one arm or functional group of a polymer component forming a covalent bond to protein. Further, in another embodiment, one arm or functional group of a polymer component may form a covalent bond with an amino acid. In one embodiment, the cross linking agents in the composition include bovine serum albumin and glutaraldehyde agent. In one embodiment, the sealant starts gelatinizing at the site within 3 seconds of application. In another embodiment, the sealant starts gelatinizing at the site within 1 minute of application. In one embodiment, the sealant compositions of the present specification act to enhance the strength of the clot matrix formed by hemostatic powder and blood and/or extrudate, bond the polymer in the sealant with tissue protein/collagen, accelerate the coagulation cascade, and/or concentrate blood and gelatinize by forming crosslinks.

Composition 3

In another embodiment, the present specification provides a third biocompatible composition, which is a sealant preferably in the form of a powder, comprising a synthetic polymer based hemostat and/or a synthetic polymer based sealant, such as a polyethylene glycol (PEG) based compound or composition. In one embodiment, polyethylene glycol (PEG) is a preferred synthetic polymer forming the core of the sealant powder and has a molecular weight in the range of about 100 to about 100,000, more preferably about 1,000 to about 20,000.

As known in the art, PEG is a material that quickly solidifies and forms a tight seal when it comes into contact with tissue. The PEG powder of the present specification works by having one or more polyethylene glycol (PEG) based polymers that rapidly crosslink with each other to form a gel. When applied to bleeding tissue, the —NH functional groups of the PEGs form covalent bonds with the protein of tissue to seal the wound.

In one embodiment, the present PEG powder helps in forming a clot matrix to bond to tissue at the bleeding site as well as to enhance the clot adhesiveness. Thus, it works both as a sealant and hemostat.

In one embodiment, the powder of the present specification is a two-part composition, comprising two different compounds, at least one of which is a polymer; the two compounds react with one another to form a covalently crosslinked gel matrix. In one embodiment, the two parts of the composition are capable of being administered separately, and rapidly form gels at the site of administration.

For example, the two reactive compounds and the gel matrix that forms when they are mixed together can be represented by the following formula:

$$\text{Compound}_1\text{-(SH)}_m\text{+Compound}_2\text{-Y}_1\rightarrow\text{Compound}_1\text{-Z-Compound}_2 \quad \text{(Formula I)}$$

Wherein, $\text{Compound}_1$ has multiple ($m\geq 2$) sulfhydryl groups (SH) that react with $\text{Compound}_2$, which has multiple ($n\geq 2$) sulfhydryl-reactive groups (Y). It should be understood that sulfhydryl groups are also "sulfhydryl reactive groups"; since it is well known that sulfhydryl groups will react with one another under certain conditions. When mixed together, the two compounds become interconnected via a covalent bond (Z).

It may be noted that individual PEG compounds may have different numbers of functional groups which may cross-link to create activated PEG formulations. For example, in one embodiment of the present composition two PEG compounds crosslink on at least one functional group of each compound to form a gel, while the resultant cross-linked PEG formulation has an available —NH functional group which covalently bonds with tissues, such as proteins. Thus, in an embodiment, the two PEG compounds crosslinking with each other may each have four available functional groups (arms)—positive and negative—that facilitate cross-linking. A cross-link may occupy at least one functional group on each PEG compound which leaves additional functional groups or arms available for bonding to another PEG molecule or other materials within the mammal. In embodiments, different quantities of each of the two compounds may be used to create activated PEG formulations with more than one cross-link that result in formulations having multiple functional groups or arms. It should be understood that such reactions may produce a heterogeneous population of activated PEG formulations. In one embodiment, the PEG compounds in the present composition have at least one functional group which bonds to protein. In one embodiment, the PEG compounds in the present composition have at least one functional group which bonds to an amino acid. Thus, the PEG compounds bond with each other on one functional group site and bond with tissue proteins on at least one other functional group site. Further, PEG compounds with any number of functional groups may be used in the powder composition of the present specification, so long as they serve the purpose of cross linking with each other and forming bonds with tissue proteins.

As described above, each of the compounds has multiple functional groups, either sulfhydryl groups or sulfhydryl-reactive groups. The non-reactive remainder of the compound is considered to be its core. At least one of the two compounds must have a polymer core in order to form an efficient gel matrix. When one of the compounds contains a polymer core, the other compound can be a small organic molecule with multiple sulfhydryl-reactive groups. However, for most applications, it is preferred for both compounds to have the same or a different polymer core.

The polymer core may be a synthetic polyamino acid, a polysaccharide, or a synthetic polymer. A preferred polymer core material is a synthetic hydrophilic polymer. Suitable synthetic hydrophilic polymers include, inter alia, polyalkylene oxide, such as polyethylene oxide ($(CH_2CH_2O)_n$), polypropylene oxide ($(CH(CH_3)CH_2O)_n$) or a polyethylene/polypropylene oxide mixture ($(CH_2CH_2O)_n$—$(CH(CH_3)CH_2O)_n$). A particularly preferred synthetic hydrophilic polymer is a polyethylene glycol (PEG) having a molecular weight within the range of about 100 to about 100,000, more preferably about 1,000 to about 20,000. More preferably still, when the polymer core is polyethylene glycol, it generally has a molecular weight within the range of about 7,500 to about 20,000. Most preferably, the polyethylene glycol has a molecular weight of approximately 10,000.

Multifunctionally activated polyalkylene oxides, such as polyethylene glycol, are commercially available, and are also easily prepared using known methods. For use as a tissue sealant, the preferred combination of activated polymers is as follows: the sulfhydry-reactive group-containing compound is the tetrafunctional PEG, pentaerythritol poly(ethylene glycol) ether tetra-succinimidyl glutarate (10,000 mol. wt.); and the sulfhydryl group-containing compound is the tetrafunctional PEG, pentaerythritol poly(ethylene glycol) ether tetra-sulfhydryl (10,000 mol. wt.). In both cases, these "four-arm" PEGs are formed by ethoxylation of pentaerythritol, where each of the four chains is approximately 2,500 mol. wt., and then undergoes derivatization to introduce the functional groups onto each of the four arms. Also preferred are analogous poly(ethylene glycol)-like compounds polymerized from di-glycerol instead of pentaerythritol.

When only one of the reactive compounds comprises a polymer core, the other reactive compound is a multi-functionally active small organic molecule. Such compounds include the di-functional di-succinimidyl esters and di-maleimidyl compounds. In addition, one of skill in the art could easily synthesize a low molecular weight multi-functional reactive compound using routine organic chemistry techniques.

In one embodiment, the bioadhesive sealant composition of the present specification in powder form comprises particles ranging in size from 0.1 micrometers to 500 micrometers, preferably in the range of 1 micrometer to 200 micrometers, and still preferably in the range of 1 micrometer to 100 micrometers.

In one embodiment, the compositions of the present specification form gels with gel times of less than 1 minute, and more preferably less than 30 seconds, and most preferably less than 15 seconds. The strength (i.e., elastic modulus or G') of the resultant gels depends on the application for which the composition is adapted, but is preferably between about 102 to 104 dynes/$cm^2$ for a soft gel, or between about 10' to 108 for a harder gel.

As described above, the biocompatible sealant powder comprises at least one PEG based compound that forms crosslinks with hemoglobin or tissue proteins (single mode composition) and forms a gel. In embodiments, the biocompatible sealant powder may comprise two PEG based compounds that react and form covalent bonds for gel forming (double mode composition). In other embodiments, more than two PEG based compounds may be used, such that they react and form bonds to form a tissue sealant gel (multi mode composition).

Blends

In another embodiment, the present specification provides a blend of two or more compositions detailed above, which is used for achieving the dual purpose of hemostasis and wound sealing. In one embodiment, a blend of modified starch based hemostatic and hydrophilic powder, and at least one or a plurality of polymer based bioadhesive sealant powder(s) is provided. In another embodiment, the blend further includes one or more clotting factors, such as albumin, thrombin, fibrin, and peptide. In another embodiment, a blend of modified starch based hemostatic and hydrophilic powder and the biocompatible sealant powder(s) described above is provided. One of ordinary skill in the art would appreciate that blends including combinations of any of the compositions provided above are within the scope of the present specification. Further, the blends may be in powder, paste or gel form.

In one embodiment, blends are obtained by mechanical mixing of the required compositions in a certain ratio. In another embodiment, blends are obtained by physical mixing of the required compositions in a certain ratio. It may be noted that the ratio of component compositions of a blend will depend on the requirements of the bleeding scenario and objectives of the application, that is, whether it is required to achieve hemostasis or sealing, or both.

For example, in a blend comprising modified starch based hemostatic and hydrophilic powder (powder A), and a polymer based bioadhesive sealant powder (powder B), the proportion of powder A may range from 5% to 95% of the total powder; and that of Powder B may be in the range of 95% to 5%. In one embodiment, the preferred range of proportion for powder A is 50% to 95%, while that of powder B is 50% to 5%. In another embodiment, the preferred range of proportion for powder A is 60% to 85%, while that of powder B is 40% to 15%.

In another embodiment, in a blend comprising modified starch based hemostatic and hydrophilic powder (powder A), and multiple polymer based bioadhesive sealant powders (powder B and powder C and Powder D), the proportion of powder A may range from 10% to 95% of the total powder; and that of Powder B may be in the range of 90% to 5%, Powder C may be in the range of 90%-5%. In one embodiment, the preferred range of proportion for powder A is 50% to 90%, while that of powder (B+C) is 50% to 10%. In another embodiment, the preferred range of proportion for powder A is 60% to 85%, while that of powder B+C is 40% to 15%.

It may be noted that in a PEG based composition, the gel forming action requires the pH to be adjusted to optimize the reaction time and to speed up gel forming. Therefore, in one embodiment, pH of the blend hemostat product is optimized by adding $NaHCO_3$ and HCl, or any other non-toxic chemical to the blend, depending upon the requirement of reaction.

In one embodiment, the components of the blend composition are mixed together chemically. For example, powder A and powder B as described above can be chemically crosslinked or grafted from one to another at the molecular level before use. This kind of chemical mixing avoids the need for the components to be physically mixed by medical professionals before use, and hence is easier to use as well as time saving when urgent hemostasis and/or wound sealing is required. Thus, in one embodiment, chemical mixing enables PEGs of powder B to form cross links to modified starch of powder A. Further, PEG function groups, can be crosslinked to starch molecular group including crosslinking to CMS and HES (hydroxyethyl starch) groups. The PEG function groups which crosslinked in (modified) starch groups can interact with hemoglobin of blood cell to accelerate the clotting cascade, as well as covalently bond to tissue collagen or proteins to achieve sealing of the wound tissue.

Since the modified starch based composition of the present specification is hydrophilic and has a high water absorption capacity, and the PEG based composition has the ability to covalently bond to tissue, combining the two compositions produces a composition having water absorption-hydrophilic properties as well as the property to covalently bond to tissue proteins having a better efficacy than using either of the above components alone.

Methods of Use

In one embodiment, the present specification provides methods of using a hemostatic powder composition in combination with a sealant gel or glue composition, such that the dual purpose of cessation of bleeding as well as wound sealing is achieved. In another embodiment, the present specification provides methods of using a hemostatic powder composition in combination with a sealant powder composition, such that the dual purpose is achieved. In yet another embodiment, present specification provides methods of using pre-mixed blends of two or more hemostatic and/or sealant compositions.

As used in the embodiments of the present specification, the degree of bleeding is categorized as "mild", "moderate" and "severe" and a qualitative definition of the same has been provided earlier in the draft.

In one embodiment, the time taken to achieve hemostasis using the biocompatible compositions of the present specification correlates with a "curing" or gel formation time of the hemostatic composition and ranges from 3 to 180 seconds after application to the bleeding site.

It may be noted that the methods described in the specification are only to describe exemplary use of the compositions of the present specification. It may also be appreciated that the following methods are flexible and may further include use of classic hemostatic techniques, such as application of gauze or manual compression in combination with the use of present compositions, depending on the requirements of the bleeding scenario.

In some embodiments, the present powder and gel compositions may be rubbed into the site of bleeding for better absorption.

Method of Use—Embodiment 1

According to a first embodiment, the biocompatible CMS or modified starch based hemostatic powder composition is used in combination with biocompatible sealant gel, both of which are described above, to achieve better efficacy than that achieved by using either of each composition alone. Also, the combination of using CMS hemostatic powder and biocompatible sealant gel/glue can achieve both effective hemostasis and tissue sealing.

FIG. 1 is a flowchart illustrating an exemplary method of use for the biocompatible hemostatic powder and sealant gel of the present specification. Referring to FIG. 1, in the first step 101, the biocompatible hydrophilic hemostatic powder is applied directly to the bleeding site. Thereafter, in the next step 102, the biocompatible sealant glue/gel is applied on the top of the powder and bleeding wound. In optional embodiments, step 102 may take place immediately, promptly, or within seconds after step 101. In embodiments, the wait time between steps 101 and 102 is dependent upon the situation or surgical practice and thus, may vary. Optionally, steps 101 and 102 may be repeated until complete hemostasis is achieved.

It may be noted that that the hemostatic powder acts to stop the bleeding, while the sealant glue applied thereafter acts to strengthen (enhance) the clot matrix and seal the wound.

Figure 2:
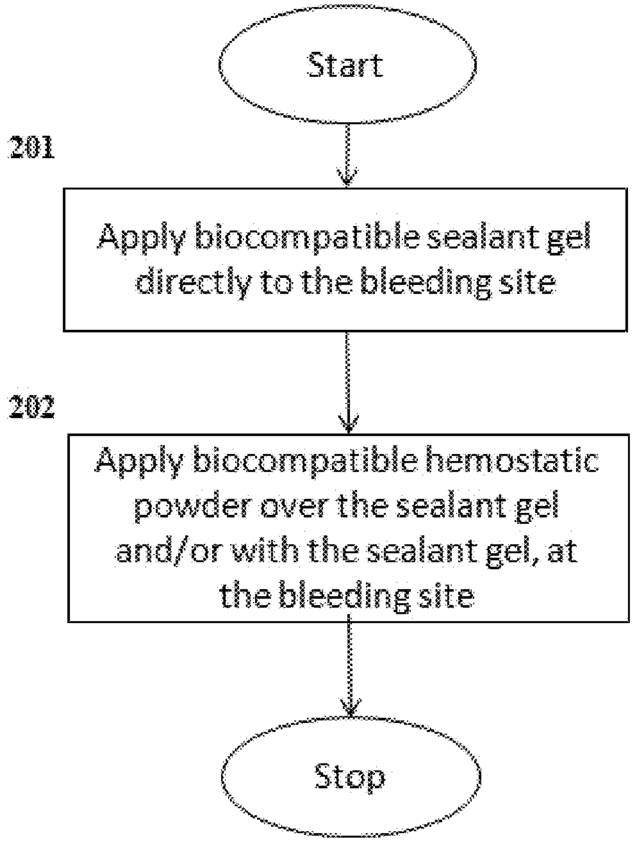
FIG. 2 is a flowchart illustrating steps for another exemplary method of use for the biocompatible hemostatic powder and sealant gel, according to an embodiment of the present specification.

Another embodiment of method of use for the biocompatible hemostatic powder and sealant gel of the present specification is illustrated in FIG. 2. Referring to FIG. 2, in the first step 201, the biocompatible tissue sealant gel is applied directly to the bleeding site. In the next step 202, the biocompatible hemostatic powder is applied on the top of the gel. In one embodiment, the hemostatic powder is applied simultaneously with the sealant, at the bleeding site. In optional embodiments, there is no or a negligible time delay between steps 201 and 202. Optionally, the steps 201 and 202 may be repeated until complete hemostasis is achieved.

Figure 3:
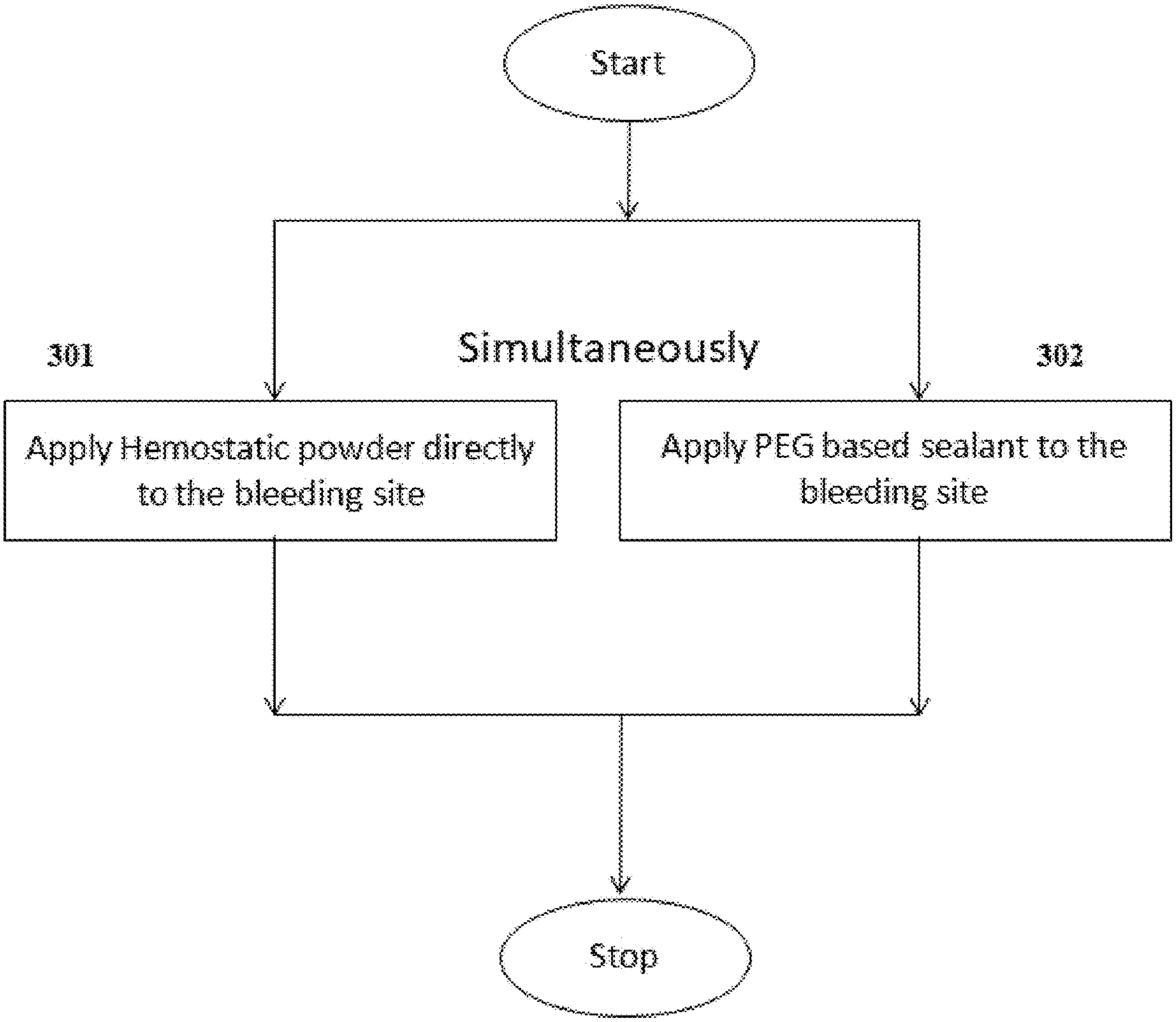
FIG. 3 is a flowchart illustrating steps for another exemplary method of use for the biocompatible hemostatic powder and sealant gel, according to an embodiment of the present specification.

FIG. 3 is a flowchart illustrating another exemplary method of use for the biocompatible hemostatic powder and sealant gel of the present specification. Referring to FIG. 3, in the first step 301, the biocompatible hydrophilic hemostatic powder is applied directly to the bleeding site. Simultaneously, in step 302, the biocompatible sealant glue/gel is applied to the bleeding site. Optionally, the powder and glue may be rubbed into the site for better absorption.

Figure 4:
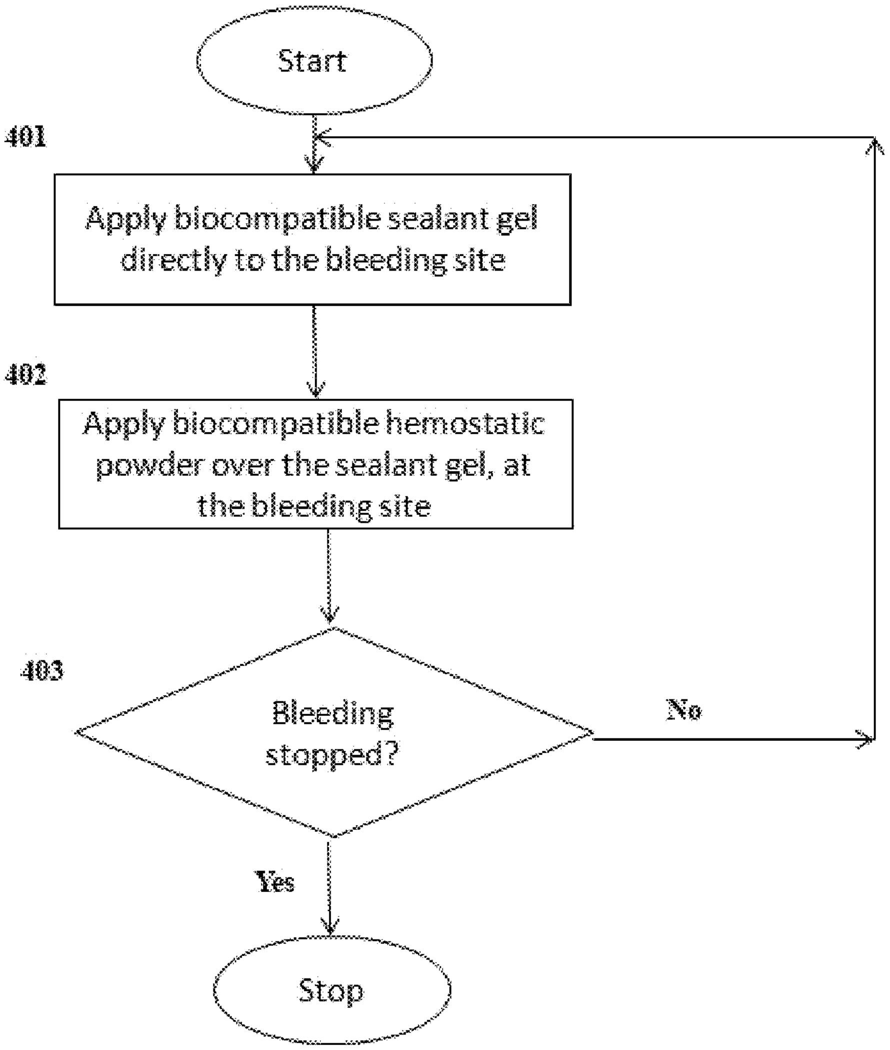
FIG. 4 is a flowchart illustrating steps for an exemplary method of use for the biocompatible hemostatic powder and sealant gel, according to an embodiment of the present specification.

FIG. 4 is a flowchart illustrating yet another embodiment of method of use for the biocompatible hemostatic powder and sealant gel of the present specification. Referring to FIG. 4, in the first step 401, biocompatible tissue sealant gel is applied directly to the bleeding site. Optionally, biocompatible hemostatic powder is first applied to the site of bleeding. Subsequently, in the next step 402, biocompatible hemostatic powder is applied on the top of the gel, if biocompatible tissue sealant gel was applied in step 401. Alternately, if biocompatible hemostatic powder was applied in step 401, then biocompatible tissue sealant gel is applied on the top of the powder in step 402. The steps 401 and 402 may be repeated until complete hemostasis is achieved, as shown in 403. Thus, this method involves alternately applying hemostatic powder followed by the sealant gel, or vice versa, as many times as required to completely stop bleeding at the site.

In one embodiment, the biocompatible hemostatic powder composition of the present specification can be directly applied or sprayed as a solution at the bleeding site, with or without the use of sealant gel. In another embodiment, the biocompatible sealant gel or glue of the present specification can be directly applied or sprayed to the bleeding wound, after application of the biocompatible hemostatic powder or simultaneously with the biocompatible hemostatic powder. In another embodiment, the biocompatible sealant gel may be mixed with the biocompatible hemostatic powder for application.

In situations where the site of bleeding is not reachable manually, or if a delivery device is the preferred mode of delivery, such as when applying to internal organs or during surgery, the biocompatible hemostatic powder and/or sealant gel of the present specification may be applied using an applicator device or an endoscopic applicator or delivery system.

Method of Use—Embodiment 2

According to a second embodiment, the biocompatible CMS or starch based hemostatic powder composition of the present specification is used in combination with biocompatible PEG based sealant powder(s) described above, to achieve better efficacy for hemostasis and wound (tissue) sealing as compared to when using either of the above composition alone.

Figure 5:
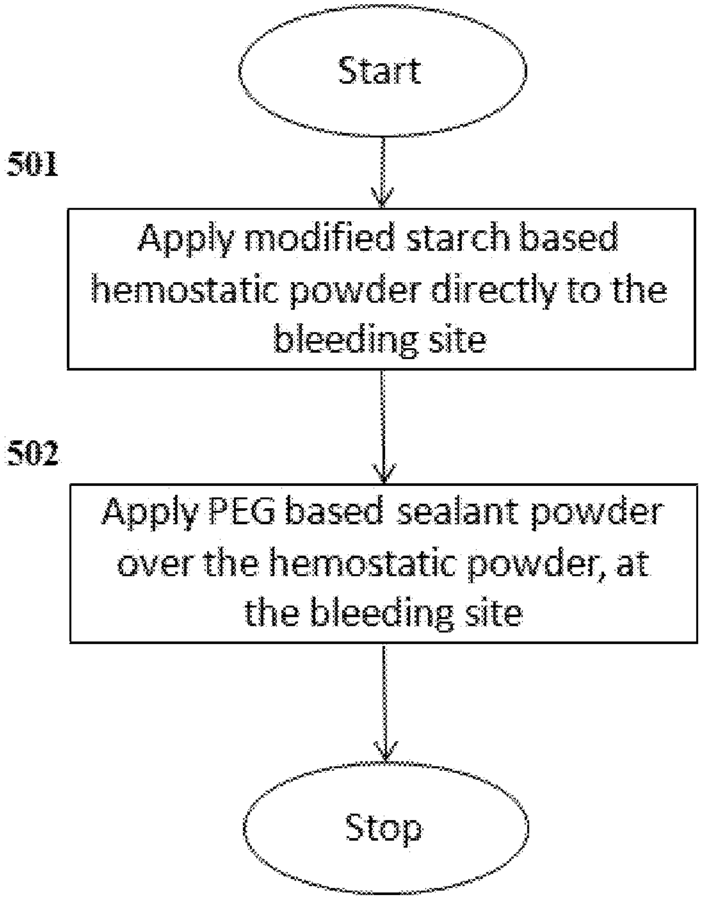
FIG. 5 is a flowchart illustrating steps for an exemplary method of use for a biocompatible modified starch based hemostatic powder and a PEG-based sealant powder, according to an embodiment of the present specification.

FIG. 5 is a flowchart illustrating an exemplary method of use for the biocompatible modified starch based hemostatic powder and PEG based sealant powder(s) of the present specification. Referring to FIG. 5, in the first step 501, the biocompatible hydrophilic hemostatic powder is applied directly to the bleeding site. Thereafter, in the next step 502, the PEG based sealant powder(s) are applied on the top of the powder and bleeding wound. In optional embodiments, step 502 may take place immediately, promptly, or within seconds after step 501. In embodiments, the wait time between steps 501 and 502 is dependent upon the situation or surgical practice and thus, may vary. Optionally, steps 501 and 502 may be repeated until complete hemostasis is achieved.

It may be noted that that the hemostatic powder acts to stop the bleeding, while the sealant powder applied thereafter acts to seal the wound and enhance clotting. In one embodiment, the hydrophilic hemostatic powder and the sealant powder(s) form a gel matrix when they come in contact with blood or extrudate of wound tissue. The process of gel formation enhances hemostasis. In this process, the components of the composition covalently bond with proteins and collagen of tissue, thereby adhering to the tissue to seal the (wound) tissue.

Figure 6:
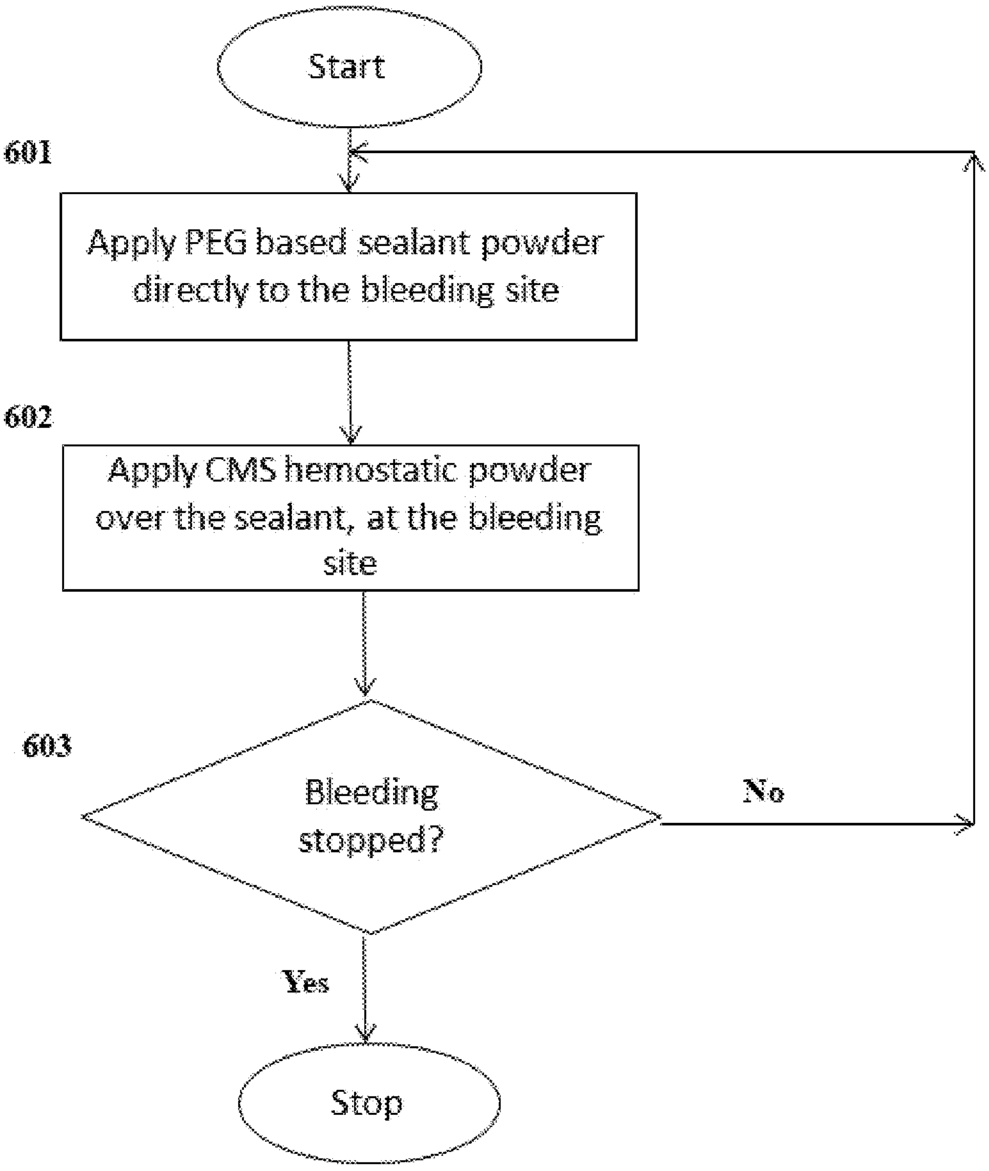
FIG. 6 is a flowchart illustrating steps for another exemplary method of use for a biocompatible modified starch based hemostatic powder and a PEG-based sealant powder (s), according to an embodiment of the present specification.

FIG. 6 is a flowchart illustrating yet another embodiment of method of use for the modified starch based biocompatible hemostatic powder and PEG based sealant powder(s) of the present specification. Referring to FIG. 6, in the first step 601, PEG based tissue sealant powder(s) is applied directly to the bleeding site. Optionally, modified starch based hemostatic powder is first applied to the site of bleeding. Subsequently, in the next step 602, modified starch based hemostatic powder is applied over the PEG based powder, if biocompatible tissue sealant powder(s) was applied first in step 601. Alternately, if modified starch based hemostatic powder was first applied in step 601, then PEG based tissue sealant powder(s) is applied over the modified starch based powder in step 602. Optionally, manual compression with gauze on the top of the powders may be applied, depending on the bleeding scenario. The steps 601 and 602 may be repeated until complete hemostasis is achieved, as shown in 603. Thus, this method involves alternately applying hemostatic powder followed by the sealant powder, or vice versa, as many times as required to completely stop bleeding at the site.

Figure 13:
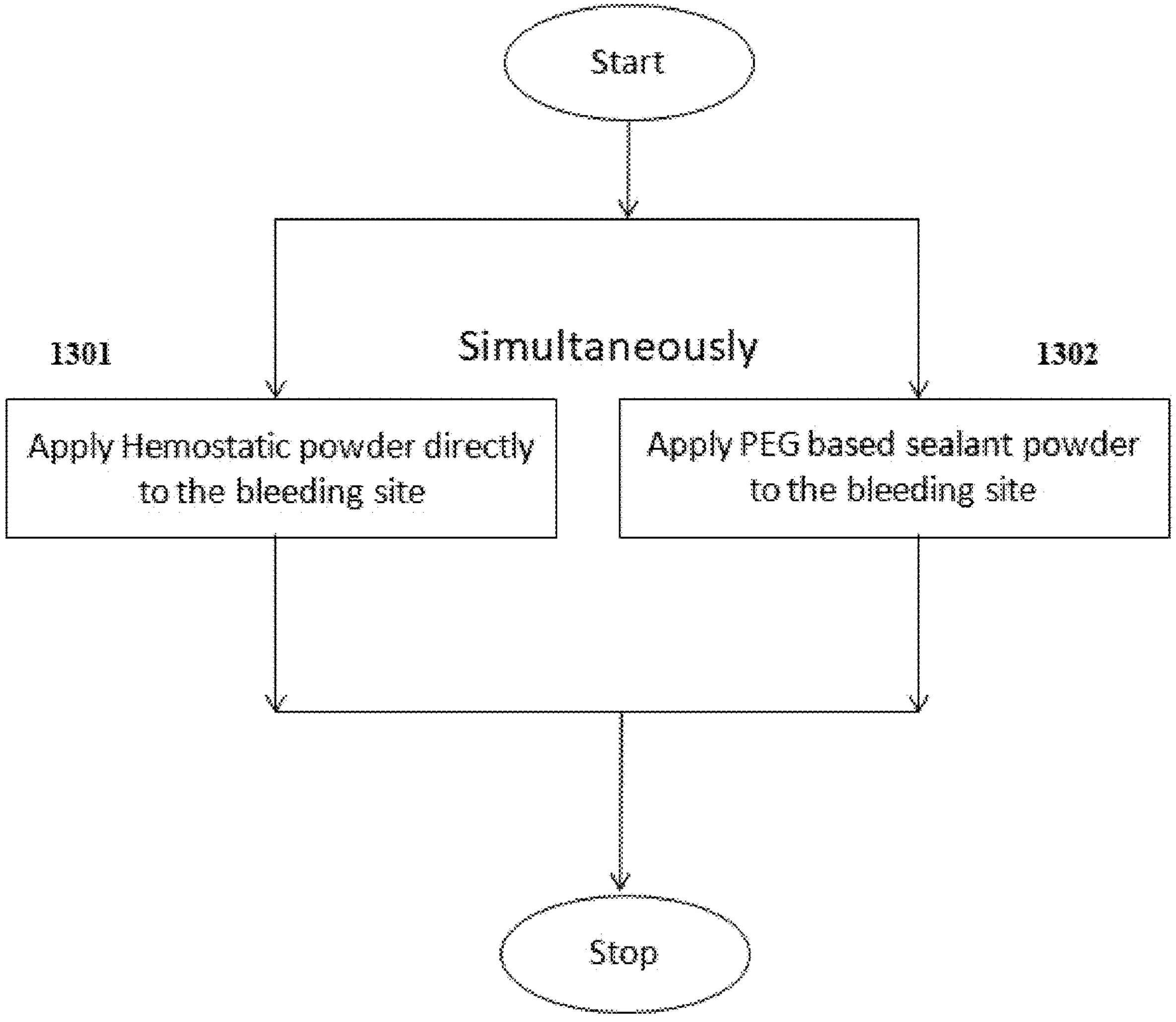
FIG. 13 is a flowchart illustrating steps for another exemplary method of use for the biocompatible hemostatic powder and sealant powder, according to an embodiment of the present specification.

In one embodiment, the modified starch based biocompatible powder composition of the present specification may be directly applied or sprayed as a solution at the bleeding site, with or without the use of the PEG based sealant powder(s). In another embodiment, the PEG based sealant powder(s) of the present specification may be directly applied or sprayed to the bleeding wound, after application of the modified starch based powder, or pre-mixing with modified starch based powder, or simultaneously with the biocompatible hemostatic powder. The latter method is illustrated in a flowchart in FIG. 13. Referring to FIG. 13, another exemplary method of use for the biocompatible hemostatic powder and sealant powder of the present specification is shown. In step 1301, the biocompatible hydrophilic hemostatic powder is applied directly to the bleeding site. Simultaneously, in step 1302, the biocompatible sealant powder is applied to the bleeding site.

Method of Use—Embodiment 3

Figure 8:
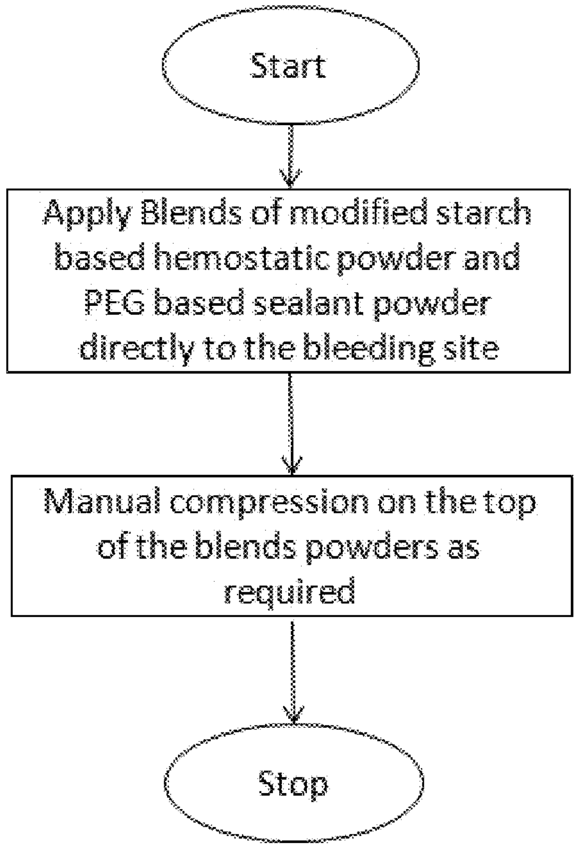
FIG. 8 is a flowchart illustrating steps for another exemplary method of use for a blend of CMS-based hemostatic powder and a PEG-based sealant powder, according to an embodiment of the present specification.

In yet another embodiment, the PEG based sealant powder(s) may be mixed with the modified starch based powder for application. The method of use for this embodiment is illustrated in the flowchart of FIG. 8. Referring to FIG. 8, in step 801 a layer of a powder comprising a blend of modified starch based biocompatible hemostatic powder and PEG based sealant powder(s) of the present specification, is applied directly to the bleeding site. Optionally in step 802, manual compression may be applied over the blend powders, as required by the situation. Steps 801 and 802 may be repeated until complete hemostasis is achieved.

In situations where the site of bleeding is not reachable manually, such as during surgery, or if a delivery device is the preferred mode of delivery, such as when applying to internal organs or during surgery, the biocompatible modified starch based powder and/or PEG based sealant powder(s) of the present specification may be applied using an applicator device or an endoscopic applicator or delivery system.

In some embodiments, blends of two or more biocompatible compositions described above may be applied directly to the site, when a blend has the ability to absorb fluid and to adhere to the tissue by forming crosslinks or covalent bonds to the tissue protein. In such cases, application involves use of a single material to achieve the dual function of hemostasis and wound sealing. This is useful in particular when moderate to severe bleeding occurs, in which cases the currently available hemostats and surgical sealants are rarely effective. In one exemplary embodiment, the single material is a combination of two PEG based compositions, preferably in powder form, which gelatinize upon coming in contact with blood/extrudate at the site of bleeding.

Exemplary Use Cases

The following are results from control experiments carried out to determine the efficacy of the blends of biocompatible hemostatic powder, biocompatible sealant gel and biocompatible sealant powder of the present specification, in comparison with other hemostats.

For the purpose of the controlled laboratory experiments, a bleeding model was created in an animal. In the present case, Bama miniature pigs were used, with the total number of pigs used for the experiment being 40, each pig weighing about 25±5 kg, and the ratio of the number of male to female pigs being 50:50. In the present case, 8-10 incisions (wounds) were created in the liver of each Bama miniature pig. Each incision had an area of the order of 2×2 $cm^2$ and a depth of approximately 0.5 cm. Blood flow rates for the lesions created in the pig liver model were recorded at specific time points and statistically analyzed. The degree of bleeding from the incision site was classified as "mild bleeding" or "oozing", "moderate bleeding", or "profuse/active/severe bleeding". A quantitative definition of degree of bleeding was derived as follows:

After the bleeding model was established, the incision site was immediately covered with dry gauze (wherein the amount of gauze is based on surgical practice) for a period of one minute, to absorb blood. The gauze was then weighed, which provided an estimate of the absorbed blood and the degree of bleeding. Using this method, the degree of bleeding was classified as 'Mild' when the weight of the absorbed blood is 0.10-1.99 grams; 'Moderate', when the weight of the absorbed blood ranges from 2.00-5.99 grams; and 'Severe', when the weight of the blood absorbed by the gauze in one minute is no less than 6.00 grams. This quantitative definition of degree of bleeding is summarized in the following table:

| | Mild Bleeding | Moderate Bleeding | Severe Bleeding |
|---|---|---|---|
| Amount of Bleeding (gram/min) | 0.10-1.99 | 2.00-5.99 | >6.00 |

In an embodiment, a qualitative definition for degree of bleeding was employed, wherein 'Mild' bleeding refers to blood oozing from a capillary; 'Moderate' bleeding is defined as when a wound site starts bleeding again immediately after wiping clean with a gauze; and 'Severe' bleeding is one which cannot be wiped clean with gauze, and needs use of a suction device. In an embodiment, bleeding is defined as above.

For the purpose of controlled laboratory experiments, the hemostasis achieved was termed as 'successful' if there was no more oozing or apparent bleeding from a wound, after the application of a hemostatic product being tested. On the other hand, if oozing, mild, moderate or severe bleeding continued from a wound after application of a hemostatic product being tested, it was termed as 'failure' of hemostasis.

In the experimental data below, the percentage of failure or success is measured using the number of incisions within each mammal tested. Therefore, by way of example, if there is a 40% success rate, then bleeding is stopped in 40% of the total number of bleeding wounds or incisions that were created in one (1) mammal. Stated differently, if 10 bleeding incisions are created in one pig, if the compounds as used in the methods of the present specification successfully stops bleeding in 7 of the 10 incisions, then the success percentage is 70%. It should be understood that in many of the scenarios, 10 incisions were created in each mammal.

The results of the controlled laboratory experiment are summarized in table in FIG. 7. The aim of the experiment was to test the efficacy of the biocompatible compositions of the present specification against known hemostatic powders, glues or gels in controlling active or severe bleeding in a pig liver bleeding model. There were seven control groups 701, 702, 703 and 704, 709, 710 and 711 in the experiment, each comprising at lease one pig and, in the present example, 40 pigs. The results were obtained for mild bleeding 711, moderate bleeding 712 and severe bleeding 713. In the first control group 701, using a single hemostatic powder, mild bleeding was controlled in 100% of the wounds or incisions of the pigs, moderate bleeding was controlled in 70% of the wounds or incisions of the pigs, while there was a 100% failure to control severe bleeding in the wounds or incisions of the pigs.

In the second control group 702, using another single hemostatic powder, mild bleeding was controlled in 100% of the wounds, moderate bleeding was controlled in 80% of the wounds, while there was a 100% failure to control severe bleeding in the wounds.

In the third control group 703, using a PEG based sealant glue, mild bleeding was controlled in 100% of the wounds or incisions, moderate bleeding was controlled in 40% of the wounds or incisions, while there was a 100% failure to control severe bleeding in the wounds or incisions of the pigs.

In a fourth control group 704, using a hemostat known as Pullulan polysaccharide, there was a 100% failure to control mild, moderate and severe bleeding in the wounds of the pigs.

In a fifth control group 709, using a only one PEG based sealant glue formulation of another brand without an additional formulation, there was a 100% failure (0% success) in controlling mild bleeding, moderate bleeding and severe bleeding in the wounds of the pigs.

In a sixth control group 710, using a hemostatic powder and a PEG based sealant glue as per the method of FIG. 2, mild bleeding, moderate bleeding, as well as severe bleeding was controlled in 100% of the wounds or incisions of the pigs. In the seventh control group 711, using PEG based powders only there was a failure to control mild bleeding, moderate bleeding and severe bleeding in 100% of the wounds or incisions of the pigs.

The experiment further comprised four test groups 705, 706, 707 and 708, where each pig was subjected to ten wounds or incisions. In the first test group 705, an exemplary biocompatible hemostatic powder was used along with the present biocompatible sealant gel, such that hemostatic powder was applied first followed by sealant gel immediately, promptly or within seconds, and this process was repeated until bleeding stopped. In the results, there was there was a 100% success in controlling mild, moderate and severe bleeding in the incisions or wounds of the pigs.

In the second test group 706, an exemplary biocompatible hemostatic powder was used followed by using the present biocompatible sealant gel. In the results, there was there was a 100% success in controlling mild, moderate and severe bleeding in the incisions or wounds of the pigs.

In the third test group 707, an exemplary biocompatible hemostatic powder was used along with the present PEG based sealant powder(s), such that a layer of hemostatic powder was applied first followed by a layer of sealant powder(s), and this process was repeated until bleeding stopped. In the results, there was there was a 100% success in controlling mild, moderate and severe bleeding in the incisions or wounds of the pigs.

In the fourth test group 708, an exemplary biocompatible hemostatic powder was used followed by using the present PEG based sealant powder(s) for curing or gel formation. In the results, there was there was a 100% success in controlling mild, moderate and severe bleeding in the incisions or wounds of the pigs.

In one embodiment, control experiments were also carried out to determine the efficacy of various blends of biocompatible hemostatic powder, biocompatible sealant gel and biocompatible sealant powder in accordance with the present specification, in comparison with other hemostats. In one embodiment, the following blends were tested, each of which is a blend of two PEG based components, with resultant blend being in glue or gel form:

1. Blend Model A1: 4arm PEG Succinimidyl Glutarate and 4arm PEG Thiol
2. Blend Model B1: 4arm PEG Succinimidyl Glutarate and 4arm PEG Amine
3. Blend Model A2: 8arm PEG Succinimidyl Glutarate and 8arm PEG Thiol
4. Blend Model B2: 8arm PEG Succinimidyl Glutarate and 8arm PEG Amine
5. Blend Model C1: 4arm PEG Maleimide and 4arm PEG Thiol
6. Blend Model C2: 4arm PEG Maleimide and 4arm PEG Amine
7. Blend Model D1: 8arm PEG Maleimide and 8arm PEG Thiol
8. Blend Model D2: 8arm PEG Maleimide and 8arm PEG Amine The following table (Table 1) details the molecular weight and structure of each PEG component used in the blends listed above:

| PEGs Name | Molecular Weight (Dalton) | Structure |
|---|---|---|
| 4arm PEG Succinimidyl Glutarate | 8000-14000 | 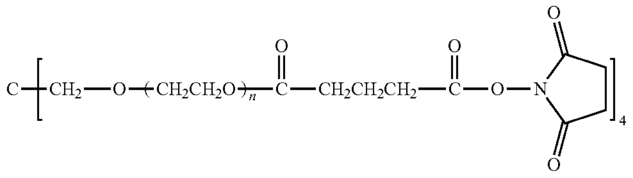 |
| 4arm PEG Thiol | 8000-14000 | $C-[CH_2-O-(CH_2CH_2O)_n-CH_2CH_2-SH]_4$ |

-continued

| PEGs Name | Molecular Weight (Dalton) | Structure |
|---|---|---|
| 4arm PEG Amine | 8000-14000 | $C-[CH_2-O-(CH_2CH_2O)_n-CH_2CH_2-NH_2HCl]_4$ |
| 4arm PEG Maleimide | 8000-14000 | 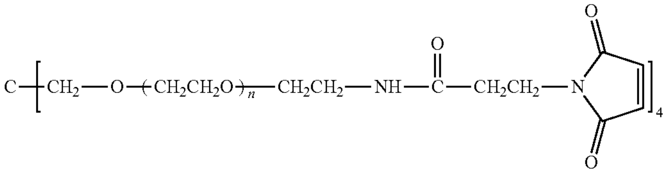 |
| 8arm PEG Succinimidyl Glutarate | 8000-14000 | 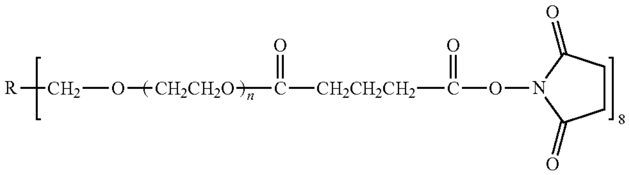 |
| 8arm PEG Thiol | 8000-14000 | $R-[CH_2-O-(CH_2CH_2O)_n-CH_2CH_2-SH]_8$ |
| 8arm PEG Amine, | 8000-14000 | $R-[CH_2-O-(CH_2CH_2O)_n-CH_2CH_2-NH_2HCl]_8$ |
| 8arm PEG Maleimide | 8000-14000 | 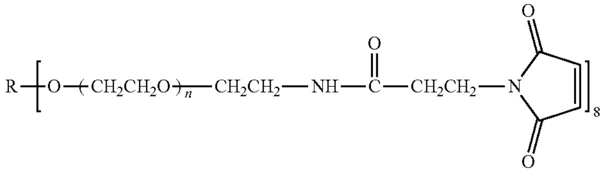 |
| Pentanedioic acid bis-(2,5-dioxo-pyrrolidin-1-yl)ester | About 10000 | Coseal A Component 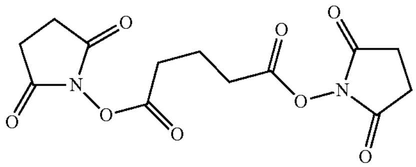 [SMILES: O=C(CCCC(=O)ON1C(=O)CCC1=O)ON1C(=O)CCC1=O] |
| A thiol terminated poly(ethylene glycol) polymer | About 10000 | Coseal B Component 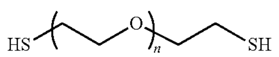 |

In one experiment, the above listed blend models were tested against a commercially available hemostat called PerClot® Polysaccharide Hemostatic System. PerClot® is a modified starch based hemostatic powder, and has a particle size of 1-1000 m, molecular weight in the range of 1500-250000 Daltons and Water Absorbency ≥12 ml/g. The above listed blend models were also tested against another commercially available hemostat called CoSeal®, which comprises a combination of Pentanedioic acid bis-(2,5-dioxo-pyrrolidin-1-yl) ester and a thiol terminated poly(ethylene glycol) polymer. FIG. 9 is a table summarizing the results for mild bleeding 901, moderate bleeding 902 and severe bleeding 903 in a control group 904 comprising 10 pigs and a test group 905 comprising 9 pigs. The table of FIG. 9 also includes the data for gel curing time (in seconds) 906 for each formulation applied to achieve hemostasis and gelation. As mentioned earlier, gel curing time refers to the time required for a glue to go from liquid to solid. For the purpose of the present experiments, gel curing time was measured by visual observation and finger contact with the surface of the glue, such that the curing time was recorded when the surface solidified.

In the control group 904, commercially available preparations PerClot® and CoSeal®, as well as the blend model compositions enlisted above were applied individually to achieve cessation of bleeding. In the test group 905, a commercially available PerClot® preparation was applied in combination with various blend model compositions enlisted above. In one experiment, commercially available preparations PerClot® and CoSeal® were applied together. As can be seen from the results of the control group 904, cessation of bleeding and sealing of the wound could not be achieved with 100% success when any of the commercial preparations or blend model compositions were applied independently. However, 100% success was achieved for all the pigs in the test group 905, for mild, moderate and even severe bleeding, as the commercial preparations were applied in combination with the blend model compositions of the present specification. Further in the test group, the gel curing time 906 was found to be significantly less compared to the pigs of control group.

In another experiment, the following powder blends were tested, each of which is a blend of two PEG based components in powder form, with the ratio of each blend component being shown in brackets:

1. P1: 4arm PEG Succinimidyl Glutarate and 4arm PEG Thiol (1:1)
2. P2: 4arm PEG Succinimidyl Glutarate and 4arm PEG Amine (1:1)
3. P3: 8arm PEG Succinimidyl Glutarate and 8arm PEG Thiol (1:1)
4. P4: 8arm PEG Succinimidyl Glutarate and 8arm PEG Amine (1:1)
5. P5: 4arm PEG Maleimide and 4arm PEG Thiol (1:1)
6. P6: 4arm PEG Maleimide and 4arm PEG Amine (1:1)
7. P7: 8arm PEG Maleimide and 8arm PEG Thiol (1:1)
8. P8: 8arm PEG Maleimide and 8arm PEG Amine (1:1)

Properties such as molecular weight and structure of each of these PEG components used in the powder blends have already been detailed in Table 1 above.

In one experiment, the above listed blend models were tested against a commercially available hemostat called PerClot® Polysaccharide Hemostatic System.

For the purpose of controlled laboratory experiment, the protocol involved applying manual compression with gauze for about 30 seconds, in case of mild, moderate or severe bleeding, followed by an observation time of 3 minutes for mild or moderate bleeding and 5 minutes for severe bleeding. Thereafter, the hemostat powder being tested was applied to the wound. In case of mild or moderate bleeding, the quantity of the powder applied was about 1 gram, and in case of severe bleeding, the quantity of the powder applied was about 2 grams. This protocol is summarized in the following table:

| Bleeding scenario | Time of manual compression with gauze | Observation time after manual compression | Total Amount of powder to apply in/on to the wound |
|---|---|---|---|
| Mild to moderate bleeding | 30 seconds | 3 minutes | 1 gram |
| Severe bleeding | 30 seconds | 5 minutes | 2 grams |

FIG. 10 is a table summarizing the results for mild bleeding 1001, moderate bleeding 1002 and severe bleeding 1003 in a control group 1004 comprising 9 pigs and a test group 1005 comprising 8 pigs.

In the control group 1004, a commercially available PerClot® preparation and the powder blend compositions enlisted above were applied individually to achieve cessation of bleeding. In the test group 1005, a commercially available PerClot® preparation was applied in combination with various powder blend compositions enlisted above. In one embodiment, for each of the powder blends used in combination with PerClot®, the ratio of PerClot® to the powder blend was 3:1. That is, PerClot® was 75% of the total amount by weight of the powders being used, and the PEG Blend was 25% of the total amount by weight of the powders being used. As can be seen from the results of the control group 1004, cessation of bleeding and sealing of the wound could not be achieved with 100% success when commercial prepared PerClot® or any of the powder blend compositions were applied independently. While PerClot® used individually was effective in controlling mild bleeding (100% success) and partially effective in controlling moderate bleeding (70% success), it showed a 100% failure in controlling severe bleeding. However, 100% success was achieved for all the pigs in the test group 1005, for mild, moderate and even severe bleeding, when the commercial preparation PerClot® was applied in combination with the present powder blend compositions. This, it can be concluded that the present powder blend compositions when used in with combination with commercial preparations such as PerClot® significantly increase the efficacy of hemostasis, especially in cases of moderate to severe bleeding, as compared to use of commercial preparations or PEGs powder independently.

In yet another embodiment, blends of modified starch based hemostatic powder and PEG based sealant powder were tested. As mentioned earlier, modified starch based compositions comprise polysaccharides with functional groups. The purpose of the present test was to observe and compare the efficacy of hemostasis when modified starch based powders (polysaccharides with functional groups) and PEG(s) based powders are applied independently versus when a modified starch based powder and a PEG(s) based powder are applied in combination. In one embodiment, the following polysaccharide powders were used for test purpose:

1. M1: Tert-amino-ethyl starch
2. M2: The aldehyde group hydroxyethyl starch
3. M3: Carbamyl ethylated carboxymethyl starch
4. M4: sulfhydryl crosslinked starch
5. M5: Thiol modified carboxymethyl cellulose (CMC-SH)
6. M6: Sulfhydryl carboxymethyl chitosan In one embodiment, the following PEG based powders were used for test purpose:

1. PA: 4arm PEG Succinimidyl Glutarate
2. PB: 4arm PEG Thiol
3. PC: 4arm PEG Amine, Properties such as molecular weight and structure of each of these PEG components have already detailed in Table 1 above.

The protocol and method followed for testing in the present case was the same as described above for testing PEG based powder blends, the results of which are summarized in the table of FIG. 10.

FIG. 11 is a table summarizing the results for mild bleeding 1101, moderate bleeding 1102 and severe bleeding 1103 in a control group 1104 comprising 9 pigs and a test group 1105 comprising 6 pigs.

In the control group 1104, the modified starch based powders and the PEG based powders enlisted above were applied individually to achieve cessation of bleeding. As can be seen from the results of the control group 1104, cessation of bleeding and sealing of the wound could not be achieved with 100% success when any of the modified starch based or PEG based powder compositions were applied independently.

In the test group 1105, the modified starch based powders and the PEG based powders enlisted above were applied in various combinations. For example, for pig1 1111, the combination used was PA(20%)+PB(10%)+M5(70%). This combination achieved 100% success for mild, moderate and severe bleeding. For pig2 1112, the combination used was PA(20%)+PC(5%)+M3(75%). This combination also achieved 100% success for mild, moderate and severe bleeding. For pig3 1113, the combination used was PA(10%)+PC(30%)+M2(60%). This combination achieved 100% success for mild and moderate bleeding, but only 20% success for severe bleeding. For pig4 1114, the combination used was PA(30%)+PB(10%)+M4(60%). This combination achieved 100% success for mild and moderate bleeding, but only 60% success for severe bleeding. For pig5 1115, the combination used was PA(30%)+PB(10%)+M6(60%). This combination achieved 100% success for mild, moderate and severe bleeding. For pig6 1116, the combination used was PA(25%)+PB(10%)+M1(65%). This combination achieved 100% success for mild and moderate bleeding, but no success in case of severe bleeding.

Thus, it can be concluded that the combined use of modified starch based hemostatic powder (polysaccharides with functional groups) and PEG based powder(s) is significantly more effective in controlling bleeding, compared to when either composition is used independently, particularly in case of moderate to severe bleeding.

From all the above experiments, it can be concluded that hemostatic powders and glue compositions, when used individually, can control oozing (mild bleeding) and sometimes moderate bleeding. However, the efficacy of these compositions, when used individually, is very low for severe bleeding. The efficacy of both the hemostasis and the sealant functions are significantly improved in combination groups—that is, when the powder and/or glue compositions of the present specification are used in combination with each other or with other commercial preparations. The success ratio for controlling severe bleeding with the used of combinations of compositions is almost 80-95%, which is remarkably better than use of hemostatic powders or glue independently.

In one embodiment, the present invention provides a kit comprising at least a hemostatic composition and at least a sealant composition, along with a delivery device or applicator. In one embodiment, the applicator includes a spraying device, which may be manual, gas assisted, mechanical, electrical, or of any other kind that suits the purpose. In one embodiment, the applicator includes separate sprayers and/or different kinds of sprayers for the hemostatic composition (such as a powder) and the sealant composition (such as a gel or glue).

In one embodiment, the present specification provides a method of applying a biocompatible hemostatic product and a biocompatible sealant product comprises the steps of passing a catheter through a channel of an endoscope, wherein the catheter is in fluid communication with two enclosed vessels and wherein said first enclosed vessel contains the first biocompatible hemostatic product and the second enclosed vessel contains the biocompatible sealant product; applying air flow pressure so as to direct said first biocompatible hemostatic product from the first vessel, through the catheter, and to said bleeding site; and applying air flow pressure so as to direct said biocompatible sealant product from the second vessel, through the catheter, and to said bleeding site.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of using a combination of a biocompatible modified starch hemostatic product and a biocompatible sealant gel to treat a bleeding wound within or on a mammal, comprising:

applying a first amount of said biocompatible modified starch hemostatic product to said bleeding wound;

waiting for a first period of time to permit the biocompatible modified starch hemostatic product to hydrate and adhere to the wound and form a first absorbent layer on the wound surface; and, applying a second amount of said biocompatible sealant gel to the bleeding wound, after formation of the first absorbent layer, wherein the biocompatible sealant gel comprises a material different from the biocompatible modified starch hemostatic product and is adapted to gelatinize in less than three minutes upon contact with the wound and to form a second sealing layer over the first absorbent layer and wherein said first amount and said second amount in combination are sufficient to cause at least one of: hemostasis in said bleeding wound, wound sealing in said wound, reducing exudation of said bleeding wound, promoting tissue healing of said wound, protecting a surface of said wound, and avoiding infection of said wound.

2. The method of claim 1, wherein said biocompatible modified starch hemostatic product comprises at least one of a carboxymethyl starch (CMS) hemostatic powder, pregelatinized modified starch hemostatic powder, gelatinized modified starch hemostatic powder, and a crosslinked carboxymethyl starch (CMS) hemostatic powder.

3. The method of claim 1, wherein said biocompatible sealant gel is a biocompatible modified starch gel.

4. The method of claim 1, wherein particle sizes of said biocompatible modified starch hemostatic powder ranges from 1-1000 micrometers, the biocompatible modified starch hemostatic powder has a molecular weight ranging from 1500-250000 Daltons, and the biocompatible modified starch hemostatic powder has a water absorbency capacity greater than or equal to 12 ml/g.

5. The method of claim 1, wherein the biocompatible sealing gel comprises a combination of pentanedioic acid bis-(2,5-dioxo-pyrrolidin-1-yl) ester and a thiol terminated poly(ethylene glycol) polymer.

6. The method of claim 1, further comprising applying the biocompatible sealant gel on top of the biocompatible modified starch hemostatic product.

7. The method of claim 1, further comprising repeating said application of the first amount and the second amount until complete hemostasis is achieved.

8. The method of claim 1, further comprising delaying said application of the biocompatible sealant gel after applying the biocompatible modified starch hemostatic product.

9. The method of claim 1, wherein said biocompatible sealant gel is adapted to gelatinize in approximately less than 3 minutes upon contact with the bleeding wound.

10. The method of claim 1, wherein the biocompatible sealant gel comprises a combination of natural hemostatic polysaccharide and synthetic hemostatic glue.

11. The method of claim 10, wherein the natural hemostatic polysaccharide comprises at least one of a biocompatible modified starch gel, a biocompatible modified starch glue, a cellulose glue and a fibrin glue.

12. The method of claim 10, wherein the synthetic hemostatic glue comprises at least one of hyaluronic acid (HA) gel, hyaluronic acid (HA) glue, polyethylene glycol (PEG) glue, polyethylene oxide (PEO) glue, synthetic polymer glue, and synthetic polymer gel.

13. The method of claim 1, wherein the bleeding wound is located in at least one of the mammal's respiratory tract, digestive tract, genital tract, and gastrointestinal tract.

14. The method of claim 1, wherein the biocompatible sealant gel comprises one or more of a sugar, a polymeric compound, and a protein.

15. The method of claim 14, wherein the sugar is at least one of a Pullulan polysaccharide, maltose, pre-gelatinized starch, Dextran, hydroxypropyl distarch phosphate, sodium carboxymethyl starch, crosslinked CMS, hydroxyethyl starch, oxidized starch, and grafted starch.

16. The method of 14, wherein the polymeric compound is at least one of N-butyl cyanoacrylate, polyethylene glycol/polyethylene oxide (PEG/PEO), polyvinyl acetate (PVA), and polyvinylpyrrolidone (PVP).

17. The method of claim 1, wherein the biocompatible sealant gel comprises two of fibrin glue, bio-glue, a polyethylene glycol (PEG) and PEG combination, carboxymethyl starch (CMS) and glycerol in combination with 5% polyvinyl acetate (PVA) solution, CMS and soybean oil in combination with 5% PVA solution, and CMS and glycerol in combination with 5% hydroxypropyl distarch phosphate (HPDSP).

* * * * *